(12) United States Patent
Doniger et al.

(10) Patent No.: US 10,108,781 B2
(45) Date of Patent: Oct. 23, 2018

(54) GLUCOSE OR KETONE BODY ANALYTE MONITORING IN VIVO

(71) Applicant: Abbott Diabetes Care Inc., Alameda, CA (US)

(72) Inventors: Kenneth J. Doniger, Menlo Park, CA (US); Gary A. Hayter, Oakland, CA (US); Scott A. Springer, San Jose, CA (US); Geoffrey V. McGarraugh, Oakland, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 548 days.

(21) Appl. No.: 14/039,758

(22) Filed: Sep. 27, 2013

(65) Prior Publication Data

US 2014/0095081 A1    Apr. 3, 2014

Related U.S. Application Data

(60) Provisional application No. 61/707,593, filed on Sep. 28, 2012.

(51) Int. Cl.
| | |
|---|---|
| *G06F 15/00* | (2006.01) |
| *G06F 19/00* | (2018.01) |
| *G16H 40/63* | (2018.01) |
| *G16H 15/00* | (2018.01) |
| *G16H 50/20* | (2018.01) |

(52) U.S. Cl.
CPC ......... *G06F 19/3406* (2013.01); *G16H 15/00* (2018.01); *G16H 40/63* (2018.01); *G16H 50/20* (2018.01)

(58) Field of Classification Search
None
See application file for complete search history.

(56) References Cited

U.S. PATENT DOCUMENTS

| | | | |
|---|---|---|---|
| 5,262,035 A | 11/1993 | Gregg et al. | |
| 5,262,305 A | 11/1993 | Heller et al. | |
| 5,264,104 A | 11/1993 | Gregg et al. | |
| 5,320,725 A | 6/1994 | Gregg et al. | |
| 5,593,852 A | 1/1997 | Heller et al. | |
| 6,175,752 B1 | 1/2001 | Say et al. | |
| 6,650,471 B2 | 11/2003 | Doi | |
| 6,746,582 B2 | 6/2004 | Heller et al. | |
| 7,811,231 B2 | 10/2010 | Jin et al. | |
| 2010/0121167 A1* | 5/2010 | McGarraugh | A61B 5/14532 600/347 |

* cited by examiner

*Primary Examiner* — G Steven Vanni
(74) *Attorney, Agent, or Firm* — Vorys, Sater, Seymour, and Pease LLP

(57) ABSTRACT

Methods, devices, and systems are provided that determine analyte trends according to different methods depending on whether a change-resistant state is active or not active. The method used when the change-resistant state is activated provides for different requirements for a resulting analyte trend to transition between states (e.g., level to non-level). Furthermore, in some aspects, methods, devices, and systems of selecting or modifying a response rate of an analyte monitoring device for an individual user are provided. User instructions for selecting or modifying a response rate of the device or system is received externally via a user interface or communication channel. The response rate of the analyte monitoring device or system is then selected or modified to the first response rate, and the device or system operated with the first response rate.

29 Claims, 10 Drawing Sheets

| | Analyte Level | Symbol | Range |
|---|---|---|---|
| 206 → | Fast Up | ↗ | beyond 2 |
| 204 → | Up | ↗ | between 1 and 2 |
| 202 → | Level | → | between negative 1 and positive 1 |
| 208 → | Down | ↘ | between negative 1 and negative 2 |
| 210 → | Fast Down | ↘ | beyond negative 2 |

|  | Initial trend state = Level<br>301 | Initial trend state = Non-level<br>302 |
|---|---|---|
| Change-Resistant State:<br>"Active"<br>303 | • Update $G_{ref}$<br>• Display level trend arrow<br>• Change-Resistant State remains active<br>325 | • If the difference between G and $G_{ref}$ is large enough<br>　• Change-Resistant State deactivated<br>　• Display non-level trend arrow<br>350<br>If not<br>　• Display level trend arrow<br>　• Change-Resistant State remains active<br>345 |
| Change-Resistant State:<br>"Not Active"<br>304 | • Change-Resistant State activated<br>• Display level trend arrow<br>• Initialize Gref<br>320 | • Display non-level trend arrow<br>• Change-Resistant State remains not-active<br>335 |

FIG. 3

GLUCOSE OR KETONE BODY ANALYTE MONITORING IN VIVO

CROSS-REFERENCE TO RELATED APPLICATIONS

This application claims priority based on U.S. Provisional Application No. 61/707,593, filed Sep. 28, 2012, the disclosures of which is incorporated by reference herein in its entirety.

BACKGROUND

In many instances it is desirable or necessary to regularly monitor the concentration of particular constituents in a fluid. A number of systems are available that analyze the constituents of bodily fluids such as blood, urine and saliva. Examples of such systems conveniently monitor the level of particular medically-significant fluid constituents, such as, for example, cholesterol, ketones, vitamins, proteins, and various metabolites or blood sugars, such as glucose. Diagnosis and management of patients suffering from diabetes mellitus, a disorder of the pancreas where insufficient production of insulin prevents normal regulation of blood sugar levels, requires carefully monitoring of blood glucose levels on a daily basis.

In vivo analyte monitoring systems include an in vivo positioned analyte sensor. At least a portion of the sensor is positioned beneath the skin surface of a user to contact bodily fluid (e.g., blood or interstitial fluid (ISF)) to monitor one or more analytes in the fluid over a period of time, and analyte monitoring is done continuously over a period of time. This is also referred to as continuous analyte monitoring in that the sensor remains positioned in the user for a continuous period of time to automatically sense an analyte. Other forms of testing include in vitro testing (also known as ex-vivo)—e.g., by withdrawing blood from a patient and applying the blood to an ex vivo test strip for insertion into a glucose meter.

In continuous analyte monitoring, trends in the rate-of-change of analyte measurements, also referred to herein as "analyte trends", are often useful to the user. For example, in addition to knowing analyte measurement levels, patients may also find analyte trends to be useful information in determining the necessity of treatment and its timing. An example of continuous analyte monitoring is continuous glucose monitoring (CGM).

Accordingly, there is a need for accurate and precise rate of change information.

SUMMARY

In some aspects of the present disclosure, methods, devices, and systems are provided that determine and/or confirm analyte trends. The methods, devices, and systems may relate, for example, to one or more components of an analyte monitoring system, such as continuous analyte monitoring system. In certain embodiments, analyte trends (also referred to as trends) are determined differently depending on whether a first analyte state is determined or a second analyte state—other states may be included as well. Trends of a first state may therefore have rules that enforce first trend criteria and trends of second state have rules that enforce second trend criteria. First and second criteria may differ by how resistant each is to change from a trend state. Resistance or movement from state to state is determined as least in part on sensor analyte data (raw or processed (e.g., calibrated). For example, a first state may be more resistant to changing from the first state to a second state, than a second state is. One state, for example, may have an additional requirement imposed, such as requiring a change in analyte values to exceed a minimum threshold for example, thus providing resistance to changes in analyte values less than the threshold. Change may be presented on a user interface, e.g., as one or more images or icons or sounds, or vibrations, the like. For example, a basic image or icon may be used to represent rate of change trend, where variations of the image or icon represents varying degrees or states at a given time. If a first analyte state is determined and represented by a first image, the first image may be more resistant to change to a second image (i.e., have rules that enforce a more strict criteria), than a second image representing a second state is.

Embodiments include analyte trends that are determined differently depending on whether a change-resistant state is active or not. When the change-resistant state is active, the trend determinations are more tolerant of, or resistant to, changes in analyte levels in certain predetermined circumstances. After in vivo derived analyte levels are received (e.g., by sensor electronics coupled to an in vivo positioned sensor, or by an analyte monitoring device in communication with the sensor electronics), initial trends may be calculated according to a trend algorithm from the in vivo derived analyte levels. Resulting analyte trends may then be determined based on the initial trends and whether the change-resistant state is active, such that when the change-resistant state is active, greater changes in analyte levels are required for a resulting analyte trend to transition from a level to non-level determination than for an initial trend to be determined as non-level. In this way, the transition of the resulting analyte trend is more tolerant of, or resistant to, changes in analyte levels than for an initial trend to be determined as non-level.

In some aspects of the present disclosure, methods, devices, and systems of selecting or modifying a response rate of an analyte monitoring device or system for an individual user are provided. An external user interface input, selector, communication channel, or the like, may be used to receive instructions for selecting or modifying a response rate of the device or system. The response rate of the analyte monitoring device or system is then selected or modified to the first response rate, and the device or system operated with the first response rate.

In some aspects of the present disclosure, methods of determining analyte trends with an analyte monitoring device are provided. The methods include receiving in vivo derived analyte measurements; calculating, with a processor, initial trends as level or non-level based on a rate-of-change for a current analyte measurement and at least one past analyte measurement. An initial trend is level when the rate-of-change is zero or within a predetermined tolerance range for zero. The method also includes determining, with the processor, whether final trends for display on a user interface are level or non-level. The final trend determinations are based on the initial trend calculations and whether a change-resistant state is active. When the change-resistant state is active, a minimum threshold of change is required between the current analyte measurement and a past analyte measurement selected as a reference in order for a final trend to transition from level to non-level. A change-resistant state is activated each time a final trend is determined to be level and deactivated each time a final trend is determined to be non-level. Further, the minimum threshold of change varies depending on the value of the current analyte measurement. Device and systems related thereto are also provided.

BRIEF DESCRIPTION OF THE DRAWINGS

A detailed description of various embodiments of the present disclosure is provided herein with reference to the accompanying drawings, which are briefly described below. The drawings are illustrative and are not necessarily drawn to scale. The drawings illustrate various embodiments of the present disclosure and may illustrate one or more embodiment(s) or example(s) of the present disclosure in whole or in part. A reference numeral, letter, and/or symbol that is used in one drawing to refer to a particular element may be used in another drawing to refer to a like element.

FIG. 3 illustrates a state table for a method of determining analyte trends with an analyte monitoring device or system, according to one embodiment.

DETAILED DESCRIPTION

Figures 1, 2:
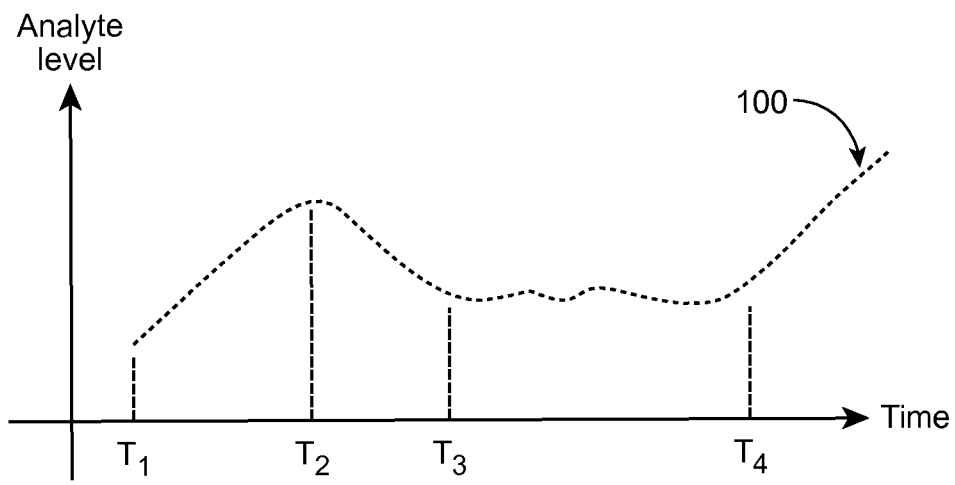
FIG. 1 illustrates a graph of analyte measurements received over time, according to one embodiment.
FIG. 2 illustrates a chart of five representative levels of glucose trends, according to one embodiment.

Before the embodiments of the present disclosure are described, it is to be understood that the present disclosure is not limited to particular embodiments described, as such may, of course, vary. It is also to be understood that the terminology used herein is for the purpose of describing particular embodiments only, and is not intended to be limiting, since the scope of the embodiments of the present disclosure will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the present disclosure. The upper and lower limits of these smaller ranges may independently be included or excluded in the range, and each range where either, neither or both limits are included in the smaller ranges is also encompassed within the present disclosure, subject to any specifically excluded limit in the stated range. Where the stated range includes one or both of the limits, ranges excluding either or both of those included limits are also included in the present disclosure.

In the description of the present disclosure herein, it will be understood that a word appearing in the singular encompasses its plural counterpart, and a word appearing in the plural encompasses its singular counterpart, unless implicitly or explicitly understood or stated otherwise. Merely by way of example, reference to "an" or "the" "analyte" encompasses a single analyte, as well as a combination and/or mixture of two or more different analytes, reference to "a" or "the" "concentration value" encompasses a single concentration value, as well as two or more concentration values, and the like, unless implicitly or explicitly understood or stated otherwise. Further, it will be understood that for any given component described herein, any of the possible candidates or alternatives listed for that component, may generally be used individually or in combination with one another, unless implicitly or explicitly understood or stated otherwise. Additionally, it will be understood that any list of such candidates or alternatives, is merely illustrative, not limiting, unless implicitly or explicitly understood or stated otherwise.

Various terms are described below to facilitate an understanding of the present disclosure. It will be understood that a corresponding description of these various terms applies to corresponding linguistic or grammatical variations or forms of these various terms. It will also be understood that the present disclosure is not limited to the terminology used herein, or the descriptions thereof, for the description of particular embodiments. Merely by way of example, the present disclosure is not limited to particular analytes, bodily or tissue fluids, blood or capillary blood, or sensor constructs or usages, unless implicitly or explicitly understood or stated otherwise, as such may vary. The publications discussed herein are provided solely for their disclosure prior to the filing date of the application. Nothing herein is to be construed as an admission that the embodiments of the present disclosure are not entitled to antedate such publication by virtue of prior invention. Further, the dates of publication provided may be different from the actual publication dates which may need to be independently confirmed.

In some aspects, the methods, devices, and systems may relate to one or more components of an analyte monitoring system, such as continuous analyte monitoring systems, including an in vivo positioned analyte sensor, sensor electronics coupled to the analyte sensor and which receive analyte sensor data from the analyte sensor, and a receiver unit that receives analyte sensor data from the sensor electronics unit. The sensor electronics unit and analyte sensor may be positioned on the body of a user, for example, and communicate analyte level data to the receiver unit. A display may also be included with the sensor electronics unit or receiver unit. Other components and devices may also be implemented in the system, such as medication delivery devices (e.g., insulin delivery devices), etc. In certain embodiment, the analyte may be, for example, glucose or a ketone body or both, and the medicine may be insulin. In various embodiments, the techniques and methods described herein may be performed by a processor in the sensor electronics, by a processor in the analyte monitoring device, or by a combination of both processors.

Trend arrows are often provided on analyte monitoring devices and systems to convey the analyte trends, but may be determined through methods that make the data unreliable or misleading in certain situations.

Further, analyte monitoring devices and systems (e.g., CGM devices and systems) provide information to users about blood glucose levels, provide information on glucose trends, and provide alarms and warning. The response rate—e.g., the amount of averaging or smoothing of the displayed data—is traditionally fixed, based on the system response and assumptions about typical user physiological characteristics, such as derived from case studies or research. However, the fixed response rate may often not be the most optimum or appropriate response rate for an individual user's physiological characteristic, or for an individual user's situation.

Trends in Analyte Measurements

The term, "analyte trends", is used herein to refer to trends in the rate-of-change or rate of the rate of change of analyte levels. For example, a positive rate-of-change is associated with analyte levels that are increasing. Therefore, the corresponding "analyte trend" may be referred to as increasing, positive, or upward, etc. Similarly, a negative rate-of-change is associated with analyte levels that are decreasing. Therefore, the corresponding "analyte trend" may be referred to as decreasing, negative, or downward, etc. With this in mind, upward and downward analyte trends may also be referred to as non-level in that "level" trends are those that have a zero slope or that fall outside a predefined tolerance range for the zero slope (e.g., +/−1 mg/di/min, or other predetermined range). The analyte levels that have a zero rate-of-change, or that have a rate-of-change falling within a predefined tolerance range, are considered to be constant and not increasing or decreasing. Therefore, the corresponding "analyte trend" may be referred to as level.

The term analyte levels (or glucose levels) is also referred to herein as "analyte measurements" (or glucose levels) or "measurements". The terms are used herein interchangeably and are not meant to be limited to a calibrated or processed analyte level. The terms may refer to both calibrated or uncalibrated analyte levels. For example, the terms may refer to raw analyte levels, such as obtained from an in vivo positioned analyte sensor, and may be equally applicable to calibrated or otherwise processed analyte levels.

FIG. 1 illustrates a graph of analyte measurements received over time, according to one embodiment. The plot of analyte measurement values include portions where the analyte measurements values are increasing over time, decreasing over time, or are remaining generally level over time. For example, the analyte measurement values between T1 and T2 are increasing over time, with a positive rate of change (i.e., a positive slope), and are thus associated with a positive analyte trend. Similarly, measurement values after T4 are increasing over time and associated with a positive analyte trend. During these times, for example, a positive analyte trend may be indicated on a user interface of an analyte monitoring device to be conveyed to a user—e.g., displaying a non-level trend arrow that points upward. Analyte measurement values between T2 and T3 are decreasing over time, with a negative rate of change (i.e., a negative slope), and are thus associated with a negative analyte trend. During these times, for example, a negative analyte trend may be indicated on a user interface of an analyte monitoring device to be conveyed to a user—e.g., displaying a non-level trend arrow that points downward.

Trends may be presented on a user interface in any variety of manners, e.g., as one or more images or icons or sounds, or vibrations, the like. For example, a basic image or icon may be displayed on the user interface and used to represent rate of change trend, where variations of the image or icon represents varying degrees or states at a given time. For example, in one embodiment, arrows may be used to represent various trend levels. For example, a horizontal arrow may indicate a level trend; an arrow pointing upwards or downwards may indicate an increasing or decreasing trend, respectively. In some instances, the steepness or degree of verticalness may be used to distinguish rapidly rising trends (e.g., more steep or vertical) than normal or slower rising trends (e.g., less steep or vertical). In some instances, the arrow may point in one direction, for example, such as to the right (e.g., upwards to the right or downwards to the right) to represent the direction in time (e.g., along a timeline).

Analyte trends may be determined, for example, by finding a rate of change of the analyte measurements, such as the difference between a current analyte measurement and a previous analyte measurement. Noise in the signal, however, may provide for inaccuracies. For instance, if one or more measurement readings (e.g., due to noise) between times, T1 and T2, were instead below the dotted line shown (i.e., the data line dips momentarily dues to the low measurement reading), then a negative trend may be briefly displayed even though the analyte measurements are generally rising overall. In some cases, to counteract this issue, the rate of change may be determined based on a larger time period between the current analyte measurement and a previous analyte measurement. For example, measurement readings may be provided every minute, for example, and the rate of change determined based on the most current measurement reading and an analyte measurement reading 10 minutes prior. Furthermore, in some embodiment, the rate of change may be determined by more than two points that are averaged (e.g., four or five points) for a smoother slope. However, a larger time period used in the trend determination may also correspond to a larger lag in response time. For example, if in the last two minutes the analyte measurement readings change from going down to going up, the trend change will not be detected right away since the trend is determined based on measurement readings from 10 minutes prior. In other embodiment, different algorithms may be used to determine the rate of change for various predetermined conditions or predetermined times—e.g., and would switch between different algorithms dynamically.

The analyte measurement values between T3 and T4 are generally level or constant, but includes slight increases or decreases over time. These slight deviations may be caused by noise in the system or simply from minor increases or decreases in the user's glucose. If, however, a system is too responsive to these slight increases or decreases of values, a positive and negative trend will be indicated on a user interface either incorrectly (e.g., from noise) or unnecessarily (e.g., from minor deviations in glucose levels). However, in certain instances it may be more beneficial to indicate a level trend to the user or user to better represent that the analyte measurement values are remaining generally at the same value. Thus, as similarly explained above, the rate of change may be determined based on a larger time period and may include averaging of a number of points to slow the responsiveness, but not without incurring a lag in response time.

Analyte trends may be indicated in a variety of manners on a user interface of an analyte monitoring device—e.g., visually and/or audibly—to show the prevailing slope of the analyte. For example, in one embodiment, analyte trends are indicated by displaying an "arrow" symbol on the user interface of an analyte monitoring device of a continuous glucose monitoring system. An upward pointing arrow (e.g., up and to the right) may represent a positive analyte trend, while a downward pointing arrow (e.g., down and to the right) may represent a negative analyte trend. Any other symbol, icon, letter, word, phrase, graphical element, image, video images, etc., may be used in other embodiments. Audible indications may be presented alone, or in addition to the visual indications, and may include sounds, tones, words, phrases, etc. The trend representations are responsive to the trend algorithms described herein.

In some instances, the number of degrees of analyte trends may vary in different embodiments, to represent the prevailing slope of the analyte measurement values. For example, FIG. 2 illustrates a chart of five levels of glucose trends, according to one embodiment. A level trend 202 is shown with a level arrow (e.g., going horizontally left to right) and includes rates of changes from negative one to positive one mg/dL per minute. A positive trend indicates analyte levels are going up and is shown with an upward arrow (e.g., pointing up and to the right). For positive trends 204 including rates of changes in the range of one to two mg/dL per minute, the positive trend is considered to be going up at a regular or typical pace. For positive trends 206 with rates of changes faster than two mg/dL per minute, the positive trend is considered to be going up fast and associated with a steeper arrow symbol (e.g., pointing up and to the right at a steeper angle, or pointing vertically up).

Similarly, negative trends 208 and 210 indicate analyte levels are going down and is shown with an downward arrow (e.g., pointing down and to the right). For negative trends 208 including rates of changes in the range of negative one to negative two mg/dL per minute, the negative trend is considered to be going down. For negative trends 210 with rates of changes faster than negative two mg/dL per minute, the negative trend is considered to be going down fast and associated with a steeper arrow symbol (e.g., pointing down and to the right at a steeper angle, or pointing vertically down).

The arrows (or other trend representations) should not be too vulnerable to clinically insignificant fluctuations, such as minute-by-minute noise or to reversals in the general trend that are not instantaneous but occur over a period of time. On the other hand, the trend arrow should not indicate an inaccurate or imprecise result—e.g., an up arrow when the glucose is actually heading downward, or vice versa. Accordingly, trend algorithms described herein provide accurate and precise trend information by analyzing analyte parameters and determining their clinical significance to trend calculation, and modulating the trend information based on the parameters.

In some aspects of the present disclosure, methods, devices, and systems are provided that determine analyte trends differently depending on whether a change-resistant state is active. When the in vivo derived analyte measurements are received, initial trends may be calculated from the in vivo derived analyte measurements. Resulting analyte trends may then be determined based on the initial trends and whether a change-resistant state is active. When the change-resistant state is active, greater changes in analyte measurements are required for a resulting analyte trend to transition from a level to non-level determination than for an initial trend to be determined as non-level. In this way, the requirements for the transition in the resulting analyte trend to occur are more tolerant of changes in the analyte measurements than the requirements implemented for the initial trend. For example, the system may be programmed to implement a method when the change-resistant state is active that may require an additional requirement, in addition to the requirements that the initial trend implements, that tolerates greater changes in analyte measurements before a transition in the trend occurs. For instance, the additional requirement may additionally require that the difference between a "current analyte measurement" and a "past analyte measurement selected as a reference" is larger than a predetermined threshold (e.g., before permitting a transition from a level trend to a non-level trend), thus making the resulting analyte trend more resistant to, or tolerant of, changes in analyte measurements than the initial trend determination. The term "current analyte measurement" is used herein to generally refer to the most recent analyte measurement being analyzed or selected for analysis, which in some embodiments is the most recent analyte measurement sampled. A "past analyte measurement" or "prior analyte measurement" refers generally to an analyte measurement preceding the "current analyte measurement" in time. The initial trend is determined based on a calculated slope, and the additional requirement discussed above is determined based on a change in analyte values between the current analyte measurement and a past analyte measurement selected as a reference.

In one embodiment, the change-resistant state is based on whether the current state of the analyte trend (i.e., the last resulting analyte trend to be determined) is "level" or "not level". The current state of the analyte trend may be, for example, the last resulting analyte trend that was displayed or otherwise indicated on the user interface. Thus, when a level arrow is indicated (e.g., displayed on the display), the current state is "level" and the change-resistant state is active. When a non-level arrow is indicated, the current state is "non-level" and the change-resistant state is not active.

FIG. 3 illustrates a state table representing a computer-implemented algorithm, for determining analyte trends, according to one embodiment. The rules or actions are dependent on two variables: whether an initial trend state is level or non-level, and whether a change-resistant state is active or not active. For example, the initial trend state may be determined, but adjusted depending on whether the change-resistant state is active or not. The resulting analyte trend may then be displayed or otherwise indicated on the user interface of an analyte monitoring device to be conveyed to the user.

Column 301 represents when the initial trend state is level—e.g., when the initial trend is determined to be level. Column 302 represents when the initial trend state is non-level (e.g., increasing or decreasing)—e.g., when the initial trend is determined to be non-level. The initial trend may be determined, for example, by a trend determination method having a large time period between the current analyte measurement and the previous analyte measurement.

Row 303 represents when the change-resistant state is active, and row 304 represents when the change-resistant state is not active. In the embodiment shown in FIG. 3, the change-resistant state is activated when the resulting analyte trend that is displayed on the user interface is level.

As shown in cell 320, when the initial trend is determined to be level, and the change-resistant state is not active, the resulting analyte trend is the same as the initial trend—i.e., level. Furthermore, the resulting trend is indicated on the user interface of an analyte monitoring device—e.g., by being displayed as a level trend arrow on the user interface—and the past analyte measurement selected as a reference (e.g., reference glucose, Gref) is initialized.

In cell 335, when the initial trend is determined to be non-level, and the change-resistant state is not active, the resulting analyte trend is the same as the initial trend—i.e., non-level. The resulting trend is indicated on the user interface of an analyte monitoring device—e.g., by being displayed as a level trend arrow on the user interface.

In cell 325, when the initial trend is determined to be level, and the change-resistant state is active, the resulting analyte trend is the same as the initial trend—i.e., level. Again, the resulting trend is indicated on the user interface of an analyte monitoring device—e.g., by being displayed as a level trend arrow on the user interface.

When the initial trend is determined to be non-level, and the change-resistant state is active, a second calculation or determination is made that ensures the resulting analyte trend is less resistant to changes in analyte measurements. For example, in blocks 345 and 350, it is determined whether the difference in analyte measurement values exceeds a predetermined threshold. Only changes larger than the threshold provide a resulting trend that is non-level. On the other hand, the resulting trend is level when the changes are not larger than the threshold, even though the initial trend determination is non-level. In this way, the resulting analyte trend is less resistant to changes in analyte measurements.

In the example shown, the difference between the most current glucose value, G, and a glucose value selected as a reference glucose value, Gref, is determined and compared to a predetermined threshold value. If the difference does not exceed the threshold value, as represented by cell 345, then the resulting analyte trend is determined to be level and indicated on the user interface of an analyte monitoring device—e.g., by being displayed as a level trend arrow on the user interface. As the resulting analyte trend is level, the change-resistant state remains active. If the difference exceeds the threshold value, as represented by cell 350, then the resulting analyte trend is determined to be non-level, and indicated on the user interface of an analyte monitoring device—e.g., by being displayed as a non-level trend arrow on the user interface. As the resulting analyte trend is now non-level, the change-resistant state is exited and no longer active.

The analyte reference value (e.g., glucose reference, Gref, in FIG. 3) may be associated with a shorter time period than the time period used to determine the initial analyte trend. For example, the initial analyte trend may be determined based on the difference of the most current analyte measurement and the analyte measurement from 15 minutes prior, while the analyte reference value (e.g., Gref in FIG. 3) may refer to a more recent analyte measurement value, such as 1 minute or 2 minutes prior to the most current analyte measurement (e.g., G in FIG. 3). In this way, the resulting analyte trend is more resistant to change (e.g., requiring a threshold difference to be exceeded), but at the same time is more responsive (e.g., being based on a shorter and more recent time period).

The difference (e.g., described in cells 345 and 350) may be expressed in various manners—e.g., absolute value of the change, average or percentage change with respect to the prior reference value, etc. Furthermore, the predetermined threshold may vary at different times, analyte levels, or other predetermined events. For example, if the current glucose value is equal to or below 100 mg/dL, then the difference is determined based on the following equation:

$$\Delta G = |G - Gref|$$

where G is the current glucose value, Gref is the prior reference glucose value, and $\Delta G$ is the difference in terms of absolute value of change. Further, if the current glucose value is above 100 mg/dL, then the difference is determined based on the following equation:

$$\Delta G = |G - Gref|/Gref$$

where G is the current glucose value, Gref is the prior reference glucose value, and $\Delta G$ is the difference in terms of percentage change with respect to prior reference value. The equations and values provided in the predetermined thresholds are exemplary and may vary in other embodiments. For example, the predetermined threshold equations and values may be selected to provide very large thresholds for glucose values that are not critical (e.g., within a user's target zone) and smaller thresholds for glucose values that are critical (e.g., hypoglycemic and/or hyperglycemic ranges).

Figure 4:
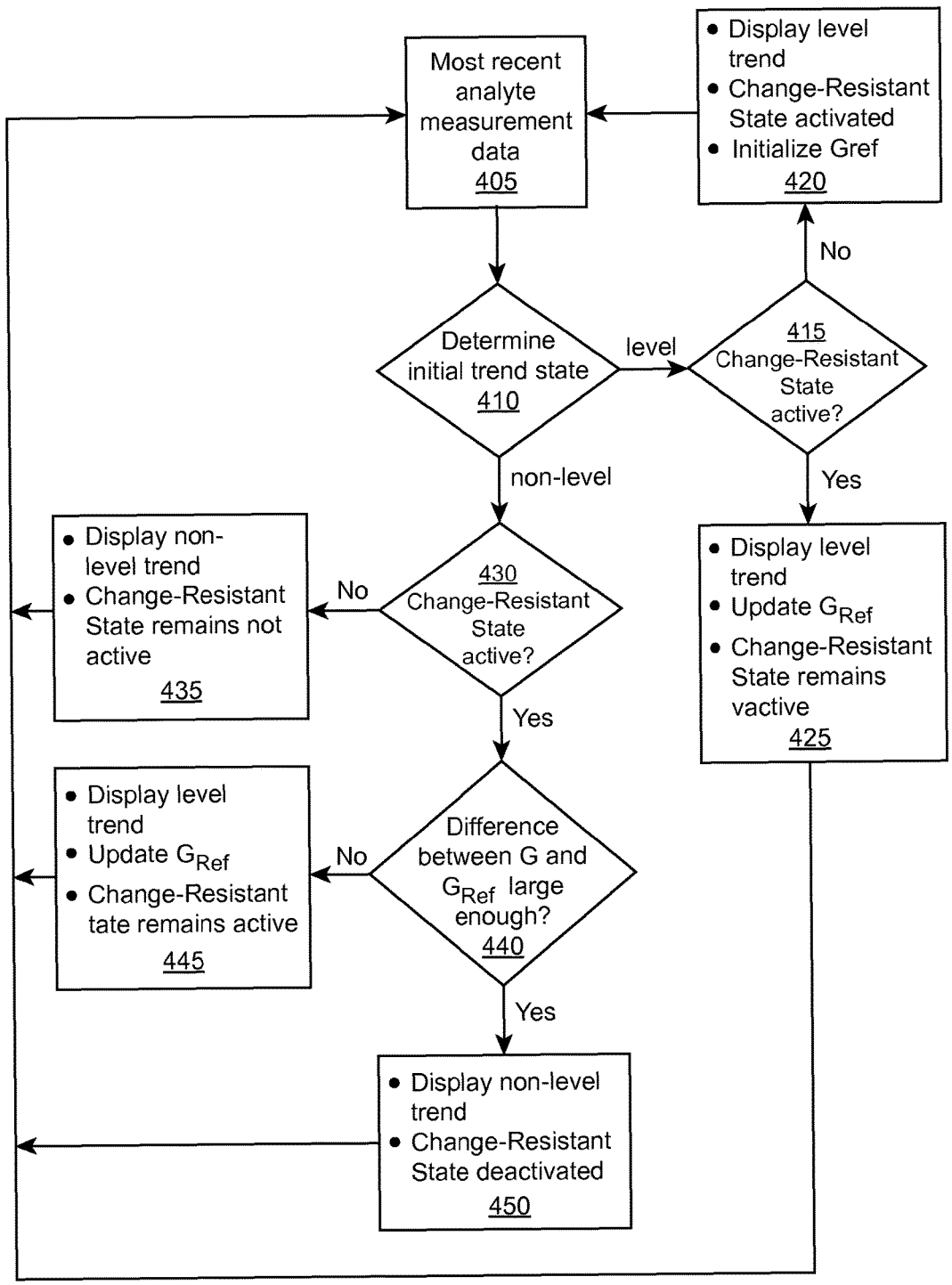
FIG. 4 illustrates a flowchart for a method embodying the state table shown in FIG. 3, according to one embodiment.

FIG. 4 illustrates a flowchart for a method embodying the state table shown in FIG. 3, according to one embodiment. The method may be implemented, for example, in an analyte monitoring device or system. For example, one or more processors or processing devices on the analyte monitoring device or system may implement the following method.

At block 405, the most recent analyte measurement data is received. The analyte measurement data may be received continuously, periodically, or intermittently, for example. The analyte measurements may be received, for example, by an analyte monitoring device or system.

The most recent analyte measurement data is used to determine the initial trend state, as represented by block 410. For example, the initial trend state may be determined by according to a trend determination method that is based off of the difference between the most recent or current analyte measurement value and a past analyte measurement value. In one embodiment, the prior analyte measurement is defined based off a large time interval with respect to the sampling interval at which the measurements are sampled—e.g., 2 times larger or greater, including as 5 times larger or greater, such as 10 times larger or greater. In this way, the analyte trend is less vulnerable to noise. For example, to avoid being too vulnerable to minute-by-minute noise, the analyte trend may be determined based on the difference of the most current analyte measurement and a past analyte measurement from 5 minutes prior or greater, for instance a 10 minutes prior, or 15 minutes prior.

If the initial trend is determined to be level, then it is determined if the change-resistant state is active or not, as represented by block 415. If the change-resistant state is active, then the resulting analyte trend is the same as the initial trend—i.e., level—as represented by block 420. Furthermore, the resulting trend is indicated on the user interface of an analyte monitoring device—e.g., by being displayed as a level trend arrow on the user interface—and the reference analyte (e.g., reference glucose, Gref) is initialized. In one embodiment, the change resistant state is activated when the resulting analyte trend becomes level. If the change-resistant state is currently not active, then the resulting analyte trend is level and indicated with the user interface—e.g., as a level trend arrow displayed on the user interface. Since the resulting analyte trend is level, the change-resistant state is activated. The resulting analyte trend and change-resistant state is then used for the next "most recent" analyte measurement to be received, as represented by the arrow returning to block 405.

If at block 415, the change-resistant state is currently active, then the resulting analyte trend is determined to be level and indicated with the user interface—e.g., as a level trend arrow displayed on the user interface. As the resulting trend arrow is level, the change-resistant state remains active, and the analyte reference (e.g., the glucose reference, Gref) is updated, as represented by block 425. This information is then used for the following calculation for the next "most recent" analyte measurement to be received, as represented by the arrow returning to block 405.

If at block 410, the initial trend is determined to be non-level, then it is determined if the change-resistant state is active or not, as represented by block 430. If the change-resistant state is not active, then the resulting analyte trend is non-level and indicated with the user interface—e.g., as a non-level trend arrow displayed on the user interface. As the resulting analyte trend is non-level, the change resistant state is not activated. This information is then used for the following calculation for the next "most recent" analyte measurement to be received, as represented by the arrow returning to block 405.

If at block 430, the change-resistant state is active, then the difference between the most recent analyte (e.g., glucose) value and a reference analyte (e.g., glucose) value is determined and compared to a threshold value, as represented by block 440. If the difference does not exceed the threshold value, then the resulting analyte trend is level and indicated to the user—e.g., as a level trend arrow displayed on the user interface—and the change-resistant state activated, as represented by block 445. This information is then used for the following calculation for the next "most recent" analyte measurement to be received, as represented by the arrow returning to block 405.

If at block 440, the difference exceeds the threshold value, then the resulting analyte trend is non-level and indicated to the user—e.g., as a non-level trend arrow displayed on the user interface, as represented by block 445. Further, the change-resistant state is deactivated since the resulting analyte trend is no longer level. This information is then used for the following calculation for the next "most recent" analyte measurement to be received, as represented by the arrow returning to block 405.

The method of FIG. 4 may be performed by, for example, an analyte monitoring device or system, such as a continuous glucose monitoring device or system. In one embodiment, the method is performed by a processor of a sensor electronics unit (also referred to as a data processing unit) coupled to an in vivo sensor. The sensor electronics unit may be a data processing device that is operably coupled to an in vivo analyte sensor. The sensor electronics unit may also include a transmitter or transceiver for data communication (e.g., analyte measurement related data) with a receiver. In another embodiment, the method is performed by a processor of a receiver that is communicably coupled to a sensor electronics unit coupled to an in vivo sensor. The term processor is used broadly herein and may include one or more processors, microprocessors, microcontrollers, other processing device, etc. In yet another embodiment, the method is performed by one or more processors in the system including a sensor electronics unit coupled to an in vivo sensor and a receiver that is communicably coupled to the sensor electronics unit. More information regarding exemplary analyte monitoring devices and systems are provided in FIGS. 10-12.

In some aspects of the present disclosure, different methods are used to determine the analyte trend depending on whether the change-resistant state is activated or not. The method used when the change-resistant state is activated provides for stricter requirements for a resulting analyte trend to transition from its current state (e.g., level to non-level) than when the change-resistant state is not activated. For example, the method used when the change-resistant state is activate may require a larger threshold of change in analyte measurement to transition from a level trend to a non-level trend, thus making the resulting analyte trend more resistant to changes in analyte measurements.

In one embodiment, the analyte trend is determined using different threshold levels, with the change-resistant state requiring a larger threshold of change to be exceeded for a non-level determination. For instance, when the change-resistant state is not activated, the analyte trend may be determined based on a threshold of zero or other negligible value, and thus any difference, or negligible difference, in analyte values (e.g., the difference between the most current analyte measurement and a prior analyte measurement) must be exceeded to yield a non-level analyte trend. On the other hand, when the change-resistant state is activated, the analyte trend determination may require a larger threshold value to be exceeded for a non-level analyte trend to result—e.g., the difference between the most current analyte measurement and a prior analyte measurement must exceed a threshold value to yield a non-level analyte trend.

For example, in one embodiment, the second determination method may require a higher threshold value to be exceeded to transition from a level to non-level trending state, than the first determination method. For instance, the threshold of the first determination method may be zero or within a predetermined tolerance range for zero, such that almost any change in slope triggers a non-level determination. On the other hand, the second determination method may include a threshold of a 5 mg/dL change in analyte level, for example, to transition from a level to non-level trending state.

In one embodiment, the analyte trend is determined using different sized time intervals. In other words, the prior analyte measurement value used in the analyte trend determination is different when the change-resistant state is activated than when not activated. For example, the prior analyte measurement value may be larger (e.g., 5 minutes prior or greater, such as 10 minutes prior or 15 minutes prior to the most current analyte measurement) when the change-resistant state is not activated, and smaller (e.g., less than 5 minutes prior, such as two minutes prior or 1 minute prior to the most current analyte measurement) when the change-resistant state is activated. In this way, the analyte trend determination is more responsive when in the change-resistant is activated. In one embodiment, the analyte trend is determined using different threshold levels and different sized time intervals. The time intervals shown are exemplary and may vary in different embodiments.

The change-resistant state may be associated with various conditions such that it activated at certain times. For example, in one embodiment, the change-resistant state is not activated or remains not active when a resulting analyte trend is "non-level" (e.g., when a "non-level" trend is indicated to a user on the user interface of an analyte monitoring device). For instance, when analyte values are increasing or decreasing (i.e., non-level), and thus analyte trending up or down, a corresponding "non-level" trending arrow or symbol is indicated on a user interface of an analyte monitoring device, and the change-resistant state is deactivated or remains not active. Because the change-resistant state is not active, the resulting analyte trends are determined according to the first determination method. On the other hand, the change-resistant state is activated when a resulting analyte trend is "level" (e.g., when a "level" trend is indicated to a user on the user interface of the analyte monitoring device). For instance, when analyte values level off, and thus analyte trend is level, a corresponding "level" trending arrow or symbol is indicated on a user interface of an analyte monitoring device, and the change-resistant state is activated or remains active. Because the change-resistant state is active, the analyte trends are determined according to the second determination method, which require larger fluctuations to transition between analyte trend states and/or are based on a more responsive time interval.

Figure 5:
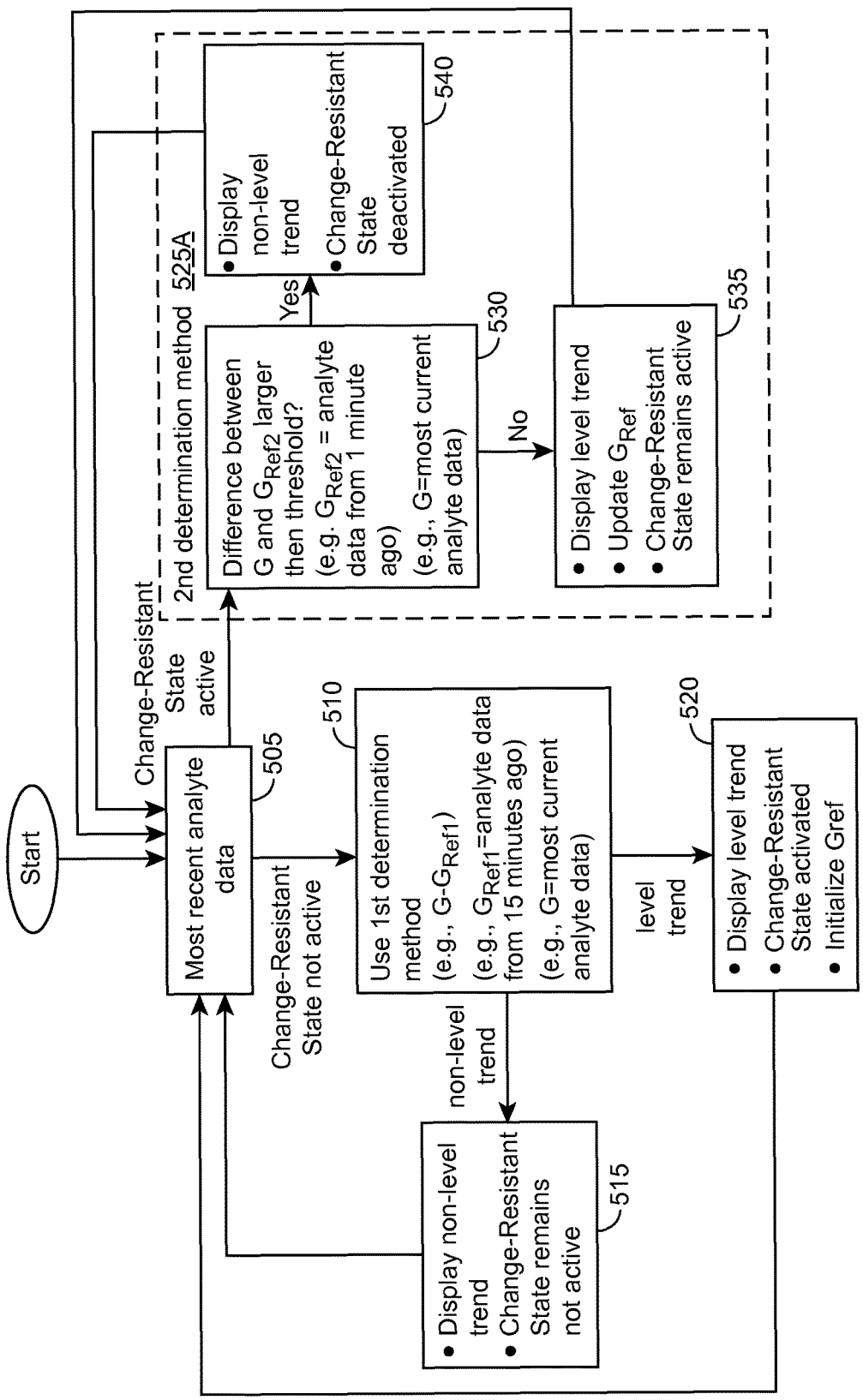
FIG. 5 illustrates a flowchart for a method of determining analyte trends with an analyte monitoring device or system, according to one embodiment.

FIG. 5 illustrates a flowchart for a method of determination analyte trends, according to one embodiment. As shown, at block 505 the most recent analyte data is received. Depending on whether the change-resistant state is activated or not, the analyte trend will be determined by either a first determination method or a second determination method.

If the change-resistant state is not active, then the first determination method is used to determine the resulting analyte trend, as represented by block 510. If the change-resistant state is active, then the second determination method is used to determine the resulting analyte trend, as represented by dotted block 525A.

In the embodiment shown, the second determination method incorporates a larger threshold to be exceeded by the difference between the most recent or current analyte (e.g., glucose) measurement value and a prior analyte (e.g., glucose) measurement value, than the first determination method. Furthermore, in the embodiment shown, the prior analyte (e.g., glucose) measurement is associated with a smaller time interval for the second determination method than for the first determination method.

For example, the first determination method shown in block 510 uses the difference between the most current glucose measurement and a glucose measurement (Gref1) 15 minutes prior to the most current glucose measurement (G) while the second determination method shown in block 530 uses the difference between the most current glucose measurement (G) and a glucose measurement (Gref2) 1 minute prior to the most current glucose measurement.

If the first determination method results in a non-level trend, then a non-level trend is indicated with the user interface (e.g., by displaying a non-level trend arrow) and the change-resistant state remains not active, as represented by block 515. If the first determination method results in a level trend, then a level trend is indicated with the user interface (e.g., by displaying a level trend arrow), the change-resistant state is activated, and the analyte reference (e.g., glucose reference, Gref) is initialized, as represented by block 520. The corresponding information from blocks 515 and 520 is then used for the following calculation for the next "most recent" analyte measurement to be received, as represented by the arrow returning to block 505.

At block 530, if the difference between the current and prior analyte measurement values does not exceed the threshold, then the resulting analyte trend is level and indicated with the user interface (e.g., by displaying a level trend arrow). As the resulting analyte trend is level, the change-resistant state remains active, and the past measurement selected as a reference (e.g., Gref2) is updated. This information is then used for the following calculation for the next "most recent" analyte measurement to be received, as represented by the arrow returning to block 505.

At block 540, if the difference between the current and prior analyte measurement values exceeds the threshold, then the resulting analyte trend is non-level and indicated with the user interface (e.g., by displaying a non-level trend arrow). As the resulting analyte trend is non-level, the change-resistant state is deactivated. This information is then used for the following calculation for the next "most recent" analyte measurement to be received, as represented by the arrow returning to block 505.

Figure 6:
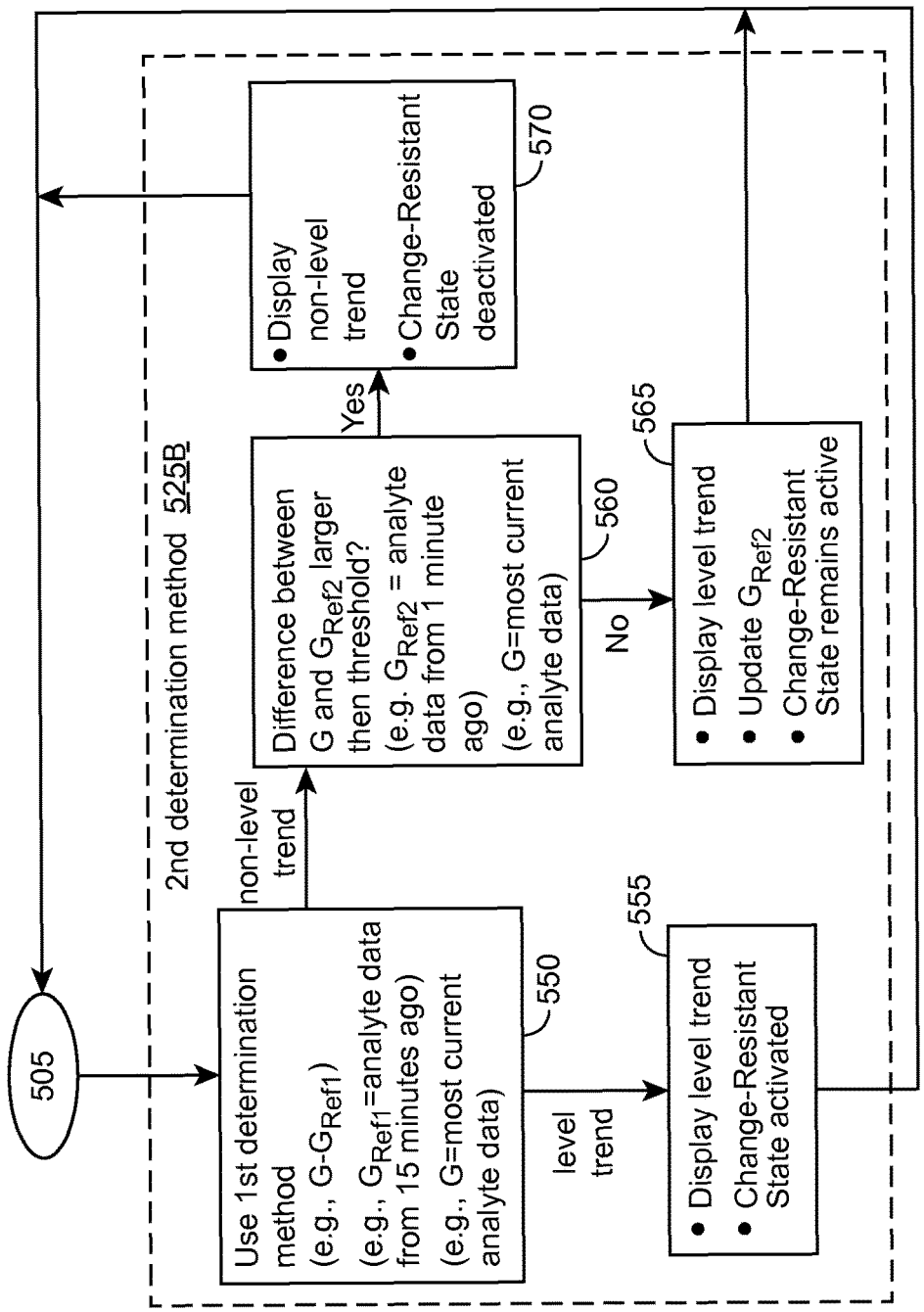
FIG. 6 illustrates a flowchart for an exemplary second determination method for the flowchart shown in FIG. 5, according to one embodiment.

In certain embodiments, the second determination method may include the first determination method. For example, FIG. 6 illustrates a flowchart for an exemplary second determination method for the flowchart shown in FIG. 5, according to one embodiment. The second determination method 525B shown in FIG. 6, for example, may be substituted for the second determination method 525A shown in FIG. 5.

As shown in FIG. 6, the most recent analyte measurement data is received at block 505 and used in the second determination method 525B. Specifically, the most recent analyte measurement data is used to first find the difference between the most recent analyte measurement data and a past measurement selected as a reference (e.g., 15 minutes prior to the most recent analyte measurement) according to the first determination method (e.g., as similarly explained in block 510 of FIG. 5). If the analyte trend is determined to be level, then to block 555 where the resulting analyte trend is level and indicated with the user interface (e.g., displayed as a level trend arrow on the user interface). If the first trend determination method yields a non-level trend, then an additional test is performed, as represented by block 560. For example, at block 560, the difference between the most current analyte measurement and a past measurement selected as a reference (e.g., 1 minute prior to the most current analyte measurement) is determined and compared to a predetermined threshold value.

If the difference between the current analyte measurement and the past measurement selected as a reference does not exceed the threshold, then the resulting analyte trend is level and indicated with the user interface (e.g., by displaying a level trend arrow), as represented by block 565. As the resulting analyte trend is level, the change-resistant state remains active, and the past measurement selected as a reference (e.g., Gref2) is updated. This information is then used for the following calculation for the next "most recent" analyte measurement to be received, as represented by the arrow returning to block 505. If the difference between the current analyte measurement and the past measurement selected as a reference exceeds the threshold, then the resulting analyte trend is non-level and indicated with the user interface (e.g., by displaying a non-level trend arrow), as represented by block 570. As the resulting analyte trend is non-level, the change-resistant state is deactivated. This information is then used for the following calculation for the next "most recent" analyte measurement to be received, as represented by the arrow returning to block 505.

Thus, despite the first determination method yielding a non-level trend, the second determination method provides an additional requirement for a non-level trend to result. The additional requirement makes a resulting non-level trend more resistant to changes in analyte measurements. It is also noted that the embodiment shown in FIG. 6 may encompass the embodiment shown in FIG. 4 in some instances.

In certain embodiments, an analyte monitoring device receives analyte measurements derived by an in vivo positioned analyte sensor. For example, the analyte monitoring device may include sensor electronics coupled to the in vivo sensor to provide samples derived by the in vivo sensor. A processor from the sensor electronics may then calculate an initial trend based on rate-of-change for a current analyte measurement and at least one past analyte measurement. The initial trend may be determined as level or non-level, and in some embodiments, more than one non-level distinction may be implemented (e.g., rising, rising rapidly, decreasing, decreasing rapidly, etc.). For example, the initial trend is determined to be level when the rate-of-change is zero, or when it is within a predetermined tolerance range for zero. For example, a tolerance range may be predetermined to be +/−1 mg/dL/min, such that any rates of change within that range result in an initial trend that is "level". If a rate-of-change falls outside the tolerance range, then the initial trend is "non-level". Multiple non-levels may be predefined with their associated ranges as well—e.g., between 1 mg/dL and 2 mg/dL defining a non-level trend for rising; and 2 mg/dL and greater defining a non-level trend for rising rapidly, etc. These values are exemplary and may vary in other embodiments.

The processor may then determine a final trend based on the initial trend calculations and whether a change-resistant state is active. The final trend is the trend that is displayed on the user interface of the analyte monitoring device so that it can be conveyed to the user. In one embodiment, the change-resistant state is activated each time a final trend is determined to be level and deactivated each time a final trend is determined to be non-level. When the change-resistant state is active, a minimum threshold of change is required between the current analyte measurement and a past analyte measurement selected as a reference in order for a final trend to transition from level to non-level.

For example, when a "level" final trend is determined and displayed to the user via the user interface, a change-resistant state is activated. An initial trend determination is made for the "next" current measurement (e.g., the next sample measurement received for analysis). If the initial trend is level, then the final trend remains level and continues to be displayed as level on the user interface, for example. If the initial trend is determined to be non-level (e.g., increasing or decreasing), then in order for the next final trend determination to also be non-level, the change in analyte value between the current analyte measurement and a past analyte measurement selected as a reference must be greater than a predetermined threshold value of change (e.g., greater than a 5 mg/dL change either positive or negative). If this additional requirement is met (e.g., the change is greater than the predetermined threshold), then the final trend is determined to be non-level and displayed to the user via the user interface, and the change-resistant state is deactivated since the final trend is now non-level. If the additional requirement is not met (e.g., the change does not exceed the predetermined threshold), then the final trend remains level and the level trend continues to be displayed to the user. In this way, when a level final trend is displayed to the user and the change-resistant state is active, the additional requirement adds an extra layer of resistance to changing the final trend to non-level. The level final trend is resistant to changes in analyte measurements that fall within the predetermined threshold, resulting in a system that is less sensitive to smaller changes when presenting a level trend to the user.

In one embodiment, the predetermine threshold varies depending on the value of the current analyte measurement. For example, as similarly described above for FIG. 3, the equations and values provided in the predetermined thresholds are exemplary and may vary in other embodiments. For example, the predetermined threshold equations and values may be selected to provide very large thresholds for glucose values that are not critical (e.g., within a user's target zone) and smaller thresholds for glucose values that are critical (e.g., hypoglycemic and/or hyperglycemic ranges).

In one embodiment, when the change resistant state is not active, then the final trend is determined to be the same as the initial trend. For example, when a "non-level" final trend is determined and displayed to the user via the user interface, then the change-resistant state either is deactivated or remains inactive. An initial trend determination is made for the "next" current measurement (e.g., the next sample measurement received for analysis). If the initial trend is determined to be non-level (e.g., increasing or decreasing), then the final trend remains non-level and continued to be displayed on the user interface. If the initial trend is level, then the final trend becomes level and displayed on the user interface and the change-resistant state is activated Variable or Selectable Response Rates Analyte monitoring devices and systems, such as continuous glucose monitoring (CGM) devices and systems, may acquire analyte measurement data over time and provide analyte measurement values for display on a user interface, for example. CGM systems can provide information to the user about blood glucose levels as well as providing information on glucose trends and provide alarms and warnings. The response rate of the system may include the frequency at which the data is displayed, the smoothing of the detected user data, the time delays for warning, alarms, and predictive alarms, etc.

Often the response is smoothed out by taking the average of a number of data points. For example, while data may be acquired minute by minute, averages may be taken over a ten minute interval or fifteen minute interval to provide a longer response time which may be less susceptible to noise for instance, but which may also result in longer lag times. CGM devices may utilize, for example, a fixed data averaging and smoothing algorithm based on compromises for system performance, hazard analyses, assumptions about patient use cases, and typical patient physiological characteristics. The amount of averaging and/or smoothing (the response rate) of the displayed data is traditionally fixed, based on general CGM system response characteristics (e.g., the rate of the absorption of glucose into the sensor) and assumptions about generalized physiological characteristics, such as an average response rate that works well for a large percentage of people. While the smoothing algorithm may be variable based on the current detected rate of blood glucose change, this is seldom an optimum solution for every patient or every monitoring situation.

In some aspects of the present disclosure, analyte monitoring devices, systems, and methods related thereto, are provided that enable external selection or modification to the system response rate—e.g., by a user, doctor, or other health care provider—to enable tailoring of the system response to an individual user's physiological characteristics or situation. In this way, the system response may be better matched to an individual user's characteristics or situation, thus allowing for more effective therapy, treatment, monitoring, etc., such as more effective medication rates, fewer false alarms, etc. Once selected, modified, or otherwise programmed by the user, doctor, or other healthcare provider, the CGM system may continuously use the resulting customized response rate when monitoring is in progress, for example.

In certain embodiments, the response rate is tailored to physiological characteristics of the first user, such as the user's individual response to medicine or analyte absorption—e.g., the user's individual response to insulin or glucose absorption. For example, it may be more useful for a system to have a fast response time when a user has a quick absorption rate of glucose. Further, the response rate may be set for a fast response rate, for example, in more intensively monitored situations such as hospital, surgery, or trauma center scenarios or procedures.

In some aspects of the present disclosure, a variable or selectable system response rate is provided. For example, the response rate may be varied for displayed data, alarms, etc. The response rate may be varied or selected, for example, via a front panel user interface or through programming over a communication connection with system or device software or firmware. For example, the front panel may be a keyboard, touchpad, touch screen display, etc. The communication connection may be any type of connection used to transmit data, such as a USB, mini USB, RS-232, Ethernet, Firewire, or other similar data communication connection. In one embodiment, the communication connection may include a wireless transceiver which communicates data wirelessly. In some instances, the response rate may be implemented as an automated algorithm in response to system conditions, such as glucose values or rates of changes of blood glucose values.

For example, the response rate may be varied by a doctor, health care provider, or by the user via the front panel of the analyte monitoring device or system, or via a remote device that communicably connects to the analyte monitoring device. The remote device may be any type of data processing device, such as a personal computer, laptop, cell phone or smart phone, personal digital assistant (PDA), etc. The response rate may be tailored, for instance, to account for the user's physiological characteristics, such as the user's response to insulin or other medications or to the user's glucose absorption. Selecting or modifying the response rate may include, for example, selecting or modifying one or more of the following: the frequency at which the data is displayed, the amount of averaging or smoothing of the analyte measurement data; and the time delay for the warning or alarm.

For example, in some instances, the response rate of the system may be modified to achieve more or less averaging in critical monitoring situations, such as during surgery or trauma scenarios. For example, in such critical monitoring situations, it may be important to know if there is a precipitous change in glucose levels. Therefore, less averaging may be desired to provide for a quicker response rate to more closely monitor the user's glucose levels to as close to real time as possible. As another example, as the rate of change of glucose may be slower during sleeping times for a user, the response rate of the system may be modified to achieve more averaging since a quick response time is not as important or critical. A user, for instance, may require a faster response time and prefer a quicker response rate during intense physical activity.

Figure 7:
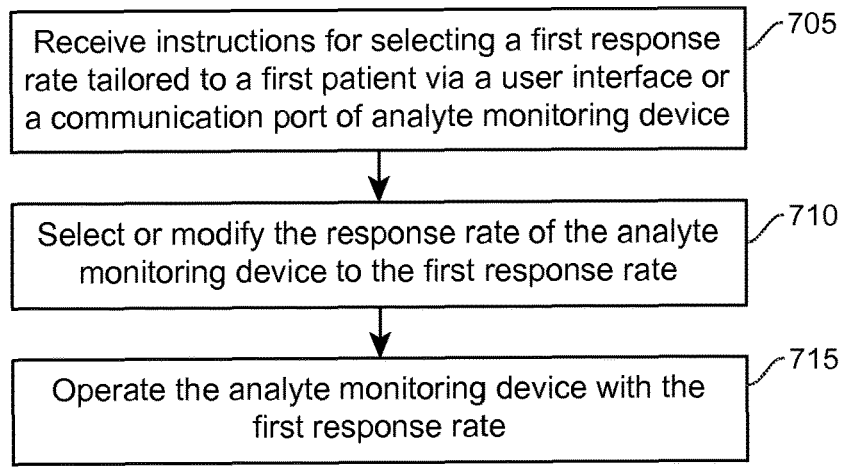
FIG. 7 illustrates a method for selecting or modifying a response rate of an analyte monitoring device for an individual user, according to one embodiment.

FIG. 7 illustrates a flowchart for a method for selecting or modifying a response rate of an analyte monitoring device or system for individual users, according to one embodiment. The method may be performed by, for example, one or more processors on an analyte monitoring device or system, such as the CGM devices and systems described herein.

At block 705, user instructions are received for selecting a response rate tailored to an individual user—e.g., to an individual user's physiological characteristics or situation. The instructions are received externally via a user interface or a communication channel of the analyte monitoring device. At block 710, the response rate of the analyte monitoring device is selected or modified to the first response rate, and at block 715, the analyte monitoring device or system is operated with the first response rate.

The selection or modification of the response rate includes selecting or modifying one or more of the following: a frequency at which data is displayed; an amount of averaging or smoothing of analyte measurement data; and a time delay for a warning or alarm. For example, the response rate of the analyte monitoring device or system may be increased by performance of one or more of the following: increasing the frequency at which the data is displayed; decreasing the amount of averaging or smoothing of the analyte measurement data; and decreasing the time delay for the warning or alarm. For instance, the first response rate may be selected or modified to increase the response rate of the analyte monitoring device or system for times associated with a user's performance of a physical activity, for a user with a quick glucose absorption rate, or for a user in a critical monitoring situation such as surgery or trauma procedure.

Figure 8:
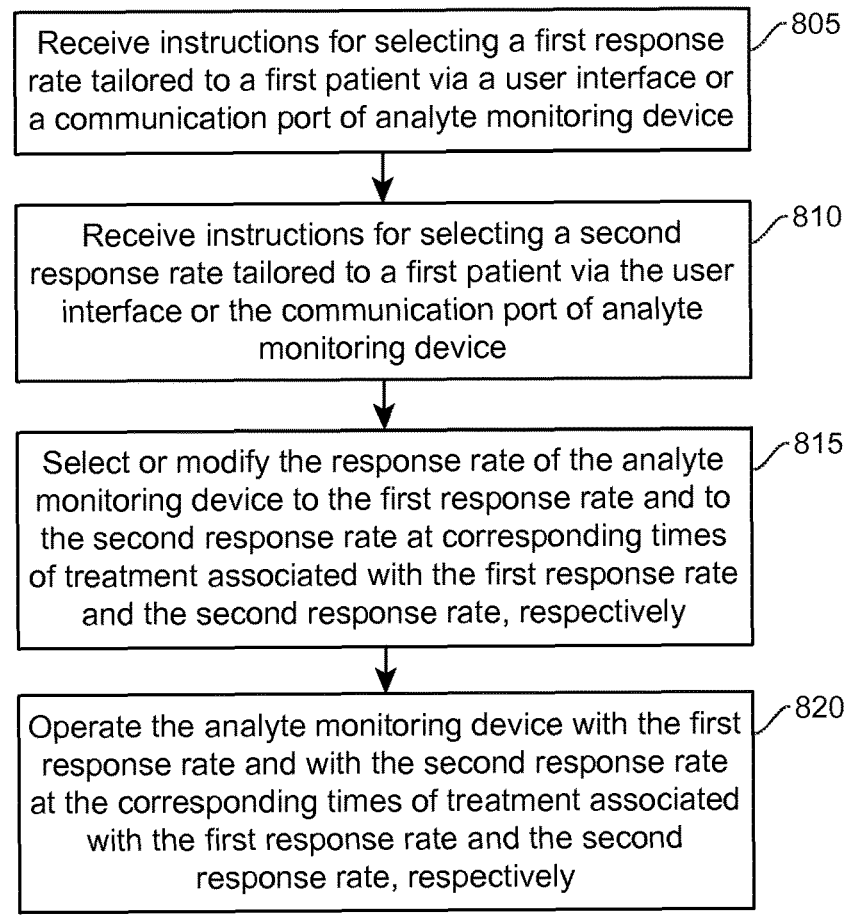
FIG. 8 illustrates flowchart for a method for selecting or modifying a response rate of an analyte monitoring device or system for individual users, according to one embodiment.

Moreover, the response rate of the analyte monitoring device or system may be decreased by performance of one or more of the following: decreasing the frequency at which the data is displayed; increasing the amount of averaging or smoothing of the analyte measurement data; and increasing the time delay for the warning or alarm. For example, the response rate may be decreased for times associated with a user's sleep patterns or events In certain embodiment, the response rate of the analyte monitoring device or system may be selected or modified differently at various times, events, or situations. A physician, healthcare provider, or user, for example, may program the various response rates for the device or system externally via a user interface or communication channel. FIG. 8 illustrates flowchart for a method for selecting or modifying a response rate of an analyte monitoring device or system for individual users, according to one embodiment.

At block 805, user instructions are received for selecting a response rate tailored to an individual user—e.g., to an individual user's physiological characteristics or situation. The instructions are received externally via a user interface or a communication channel of the analyte monitoring device. At block 810, user instructions are received for selecting a different response rate tailored to an individual user—e.g., to an individual user's physiological characteristics or situation. The instructions are again received externally via a user interface or a communication channel of the analyte monitoring device. The user instructions at blocks 805 and 810 may be provided at the same time—e.g., during a single visit to a physician—or at different times—e.g., the first user instructions at a first visit and the second user instructions at follow-up visit.

At block 815, the response rate of the analyte monitoring device or system is selected or modified to the first response rate at the corresponding times or situations defined in block 805, while the response rate of the analyte monitoring device or system is selected or modified to the second response rate at the corresponding times and situations defined in block 810. Furthermore, at block 820, the analyte monitoring device or system is operated with the first response rate at the corresponding times or situations defined in block 805, and operated with the second response rate at the corresponding times or situations defined in block 810.

The analyte monitoring device or system may continuously use the resulting customized response rate when monitoring is in progress. In some instances, the first and second user instructions at block 805 and 810 are programmed on the device or system at the same time, or otherwise implemented to exist simultaneously on the device or system. In such case, the analyte monitoring device or system is operated with the first response rate and second response rate at the corresponding times or situations while monitoring is in progress. In some instances, the second instructions at block 810 may be programmed on the device or system to override the first user instructions at block 805. In such case, the analyte monitoring device or system is operated with the second response rate after the second instructions are received.

Figure 9:
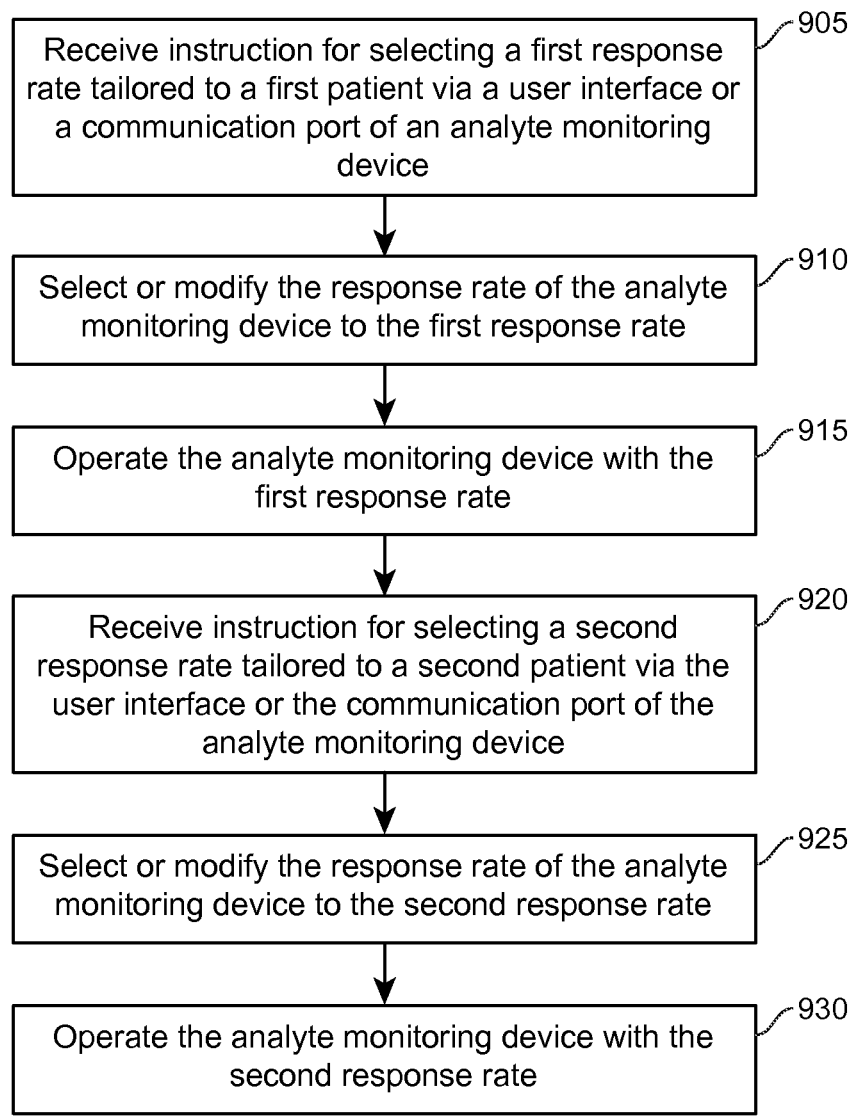
FIG. 9 illustrates a flowchart for a method for selecting or modifying a response rate of an analyte monitoring device or system for individual users, according to one embodiment.

In some aspects, an analyte monitoring device or system may be used with multiple users, such as in a hospital environment where a nurse or healthcare professional monitors multiple users at one time. In such case, the analyte monitoring device or system may be tailored differently for each individual user. FIG. 9 illustrates a flowchart for a method for selecting or modifying a response rate of an analyte monitoring device or system for individual users, according to one embodiment.

At block 905, user instructions are received for selecting or modifying a response rate tailored to an individual user—e.g., to an individual user's physiological characteristics or situation. The instructions are received externally via a user interface or a communication channel of the analyte monitoring device or system. At block 910, the response rate of the analyte monitoring device is selected or modified to the first response rate, and at block 915, the analyte monitoring device or system is operated with the first response rate.

At block 920, user instructions are received for selecting or modifying a response rate tailored to a different individual user than at block 905. The instructions are also received externally via a user interface or a communication channel of the analyte monitoring device or system. At block 925, the response rate of the analyte monitoring device is selected or modified to the second response rate, and at block 930, the analyte monitoring device or system is operated with the second response rate.

In some embodiments, the user instructions may be received each time before the device or system is used with a new user. For example, the nurse or healthcare practitioner may enter user instructions for selecting a specific response rate for each user before operating the device or system with the corresponding response rate for the user. In some embodiments, the analyte monitoring device or system may be programmed with specific response rates for multiple users via the user interface or communication channel. In some instances, the nurse or healthcare practitioner may enter the user identification code or scan the user's identification code, for example, to select or modify the response rate for the device or system for the specific user.

Example Analyte Monitoring Devices and Systems

Embodiments of the present disclosure relate to methods, devices, and systems for detecting at least one analyte, including glucose, in body fluid. Embodiments relate to the continuous, periodic, and intermitted) in vivo monitoring of the level of one or more analytes using a continuous or on-demand analyte monitoring device or system. The system may include an analyte sensor at least a portion of which is to be positioned beneath a skin surface of a user for a period of time. The present disclosure may also be applicable to discrete monitoring of one or more analytes using an in vitro blood glucose ("BG") meter and an analyte test strip.

Embodiments include combined or combinable devices, systems and methods and/or transferring data between an in vivo continuous system and an in vivo system. In one embodiment, the systems, or at least a portion of the systems, are integrated into a single unit.

For example, the analyte monitoring devices and systems may include, or communicate with, an analyte sensor at least a portion of which is positionable beneath the skin surface of the user for the in vivo detection of an analyte, including glucose, lactate, and the like, in a body fluid. Embodiments include wholly implantable analyte sensors and analyte sensors in which only a portion of the sensor is positioned under the skin and a portion of the sensor resides above the skin, e.g., for contact to a sensor control unit (which may include a communication module, e.g., a transmitter or the like), a receiver/display unit, transceiver, processor, etc. The in vivo positioned sensor may be, for example, subcutaneously positionable in a user for the continuous, periodic, or on-demand monitoring of a level of an analyte in the user's interstitial fluid.

In one embodiment, an analyte sensor may be positioned in contact with interstitial fluid to detect the level of glucose, which detected glucose may be used to infer the glucose level in the user's bloodstream. Embodiments of the analyte sensors may be configured for monitoring the level of the analyte over a time period which may range from seconds, minutes, hours, days, weeks, to months, or longer.

In one embodiment, the analyte sensors, such as glucose sensors, are capable of in vivo detection of an analyte for one hour or more, e.g., a few hours or more, e.g., a few days or more, e.g., three or more days, e.g., five days or more, e.g., seven days or more, e.g., several weeks or more, or one month or more.

As demonstrated herein, the methods of the present disclosure are useful in connection with a device that is used to measure or monitor an analyte (e.g., glucose), such as any such device described herein. These methods may also be used in connection with a device that is used to measure or monitor another analyte (e.g., ketones, ketone bodies, HbA1c, and the like), including oxygen, carbon dioxide, proteins, drugs, or another moiety of interest, for example, or any combination thereof, found in bodily fluid, including subcutaneous fluid, dermal fluid (sweat, tears, and the like), interstitial fluid, or other bodily fluid of interest, for example, or any combination thereof.

Figure 10:
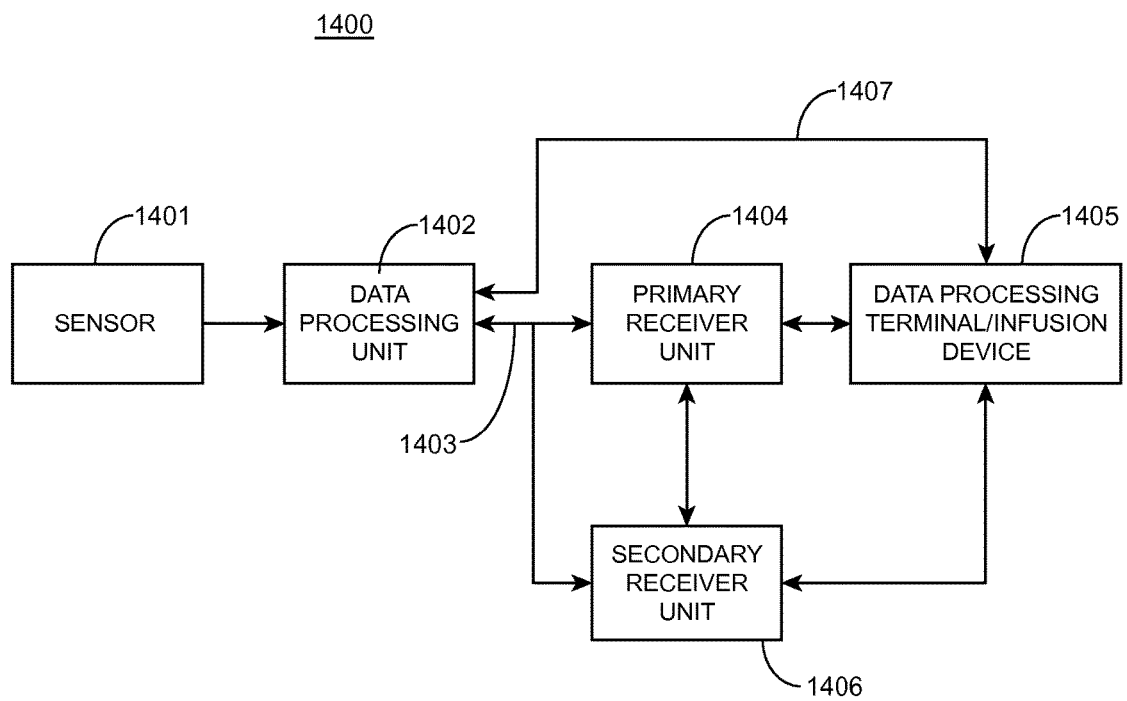
FIG. 10 shows an analyte (e.g., glucose) monitoring system, according to one embodiment.

FIG. 10 shows an analyte (e.g., glucose) monitoring system, according to one embodiment. Aspects of the subject disclosure are further described primarily with respect to glucose monitoring devices and systems, and methods of glucose detection, for convenience only and such description is in no way intended to limit the scope of the embodiments. It is to be understood that the analyte monitoring system may be configured to monitor a variety of analytes at the same time or at different times.

Analytes that may be monitored include, but are not limited to, acetyl choline, amylase, bilirubin, cholesterol, chorionic gonadotropin, glycosylated hemoglobin (HbA1c), creatine kinase (e.g., CK-MB), creatine, creatinine, DNA, fructosamine, glucose, glucose derivatives, glutamine, growth hormones, hormones, ketones, ketone bodies, lactate, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be monitored. In embodiments that monitor more than one analyte, the analytes may be monitored at the same or different times.

The analyte monitoring system 1400 includes an analyte sensor 1401, a data processing unit 1402 connectable to the sensor 1401, and a primary receiver unit 1404. In some instances, the primary receiver unit 1404 is configured to communicate with the data processing unit 1402 via a communication link 1403. In one embodiment, the primary receiver unit 1404 may be further configured to transmit data to a data processing terminal 1405 to evaluate or otherwise process or format data received by the primary receiver unit 1404. The data processing terminal 1405 may be configured to receive data directly from the data processing unit 1402 via a communication link 1407, which may optionally be configured for bi-directional communication. Further, the data processing unit 1402 may include a transmitter or a transceiver to transmit and/or receive data to and/or from the primary receiver unit 1404 and/or the data processing terminal 1405 and/or optionally a secondary receiver unit 1406.

Also shown in FIG. 10 is an optional secondary receiver unit 1406 which is operatively coupled to the communication link 1403 and configured to receive data transmitted from the data processing unit 1402. The secondary receiver unit 1406 may be configured to communicate with the primary receiver unit 1404, as well as the data processing terminal 1405. In one embodiment, the secondary receiver unit 1406 may be configured for bi-directional wireless communication with each of the primary receiver unit 1404 and the data processing terminal 1405. As discussed in further detail below, in some instances, the secondary receiver unit 1406 may be a de-featured receiver as compared to the primary receiver unit 1404, for instance, the secondary receiver unit 1406 may include a limited or minimal number of functions and features as compared with the primary receiver unit 1404. As such, the secondary receiver unit 1406 may include a smaller (in one or more, including all, dimensions), compact housing or embodied in a device including a wrist watch, arm band, PDA, mp3 player, cell phone, etc., for example. Alternatively, the secondary receiver unit 106 may be configured with the same or substantially similar functions and features as the primary receiver unit 1404. The secondary receiver unit 106 may include a docking portion configured to mate with a docking cradle unit for placement by, e.g., the bedside for night time monitoring, and/or a bi-directional communication device. A docking cradle may recharge a power supply.

Only one analyte sensor 1401, data processing unit 1402 and data processing terminal 1405 are shown in the embodiment of the analyte monitoring system 1400 illustrated in FIG. 10. However, the analyte monitoring system 1400 may include more than one sensor 1401 and/or more than one data processing unit 1402, and/or more than one data processing terminal 1405. Multiple sensors may be positioned in a user for analyte monitoring at the same or different times.

The analyte monitoring system 1400 may be a continuous monitoring system, or semi-continuous, or a discrete monitoring system. In a multi-component environment, each component may be configured to be uniquely identified by one or more of the other components in the system so that communication conflict may be readily resolved between the various components within the analyte monitoring system 1400. For example, unique IDs, communication channels, and the like, may be used.

In one embodiment, the sensor 1401 is physically positioned in or on the body of a user whose analyte level is being monitored. The sensor 1401 may be configured to at least periodically sample the analyte level of the user and convert the sampled analyte level into a corresponding signal for transmission by the data processing unit 1402. The data processing unit 1402 is coupleable to the sensor 1401 so that both devices are positioned in or on the user's body, with at least a portion of the analyte sensor 1401 positioned in vivo. The data processing unit may include a fixation element, such as an adhesive or the like, to secure it to the user's body. A mount (not shown) attachable to the user and mateable with the data processing unit 1402 may be used. For example, a mount may include an adhesive surface. The data processing unit 1402 performs data processing functions, where such functions may include, but are not limited to, filtering and encoding of data signals, each of which corresponds to a sampled analyte level of the user, for transmission to the primary receiver unit 1404 via the communication link 1403. In one embodiment, the sensor 1401 or the data processing unit 1402 or a combined sensor/data processing unit may be wholly implantable under the skin surface of the user.

In one embodiment, the primary receiver unit 1404 may include an analog interface section including an RF receiver and an antenna that is configured to communicate with the data processing unit 1402 via the communication link 1403, and a data processing section for processing the received data from the data processing unit 1402 including data decoding, error detection and correction, data clock generation, data bit recovery, etc., or any combination thereof.

In operation, the primary receiver unit 1404 in one embodiment is configured to synchronize with the data processing unit 1402 to uniquely identify the data processing unit 1402, based on, for example, an identification information of the data processing unit 1402, and thereafter, to periodically receive signals transmitted from the data processing unit 1402 associated with the monitored analyte levels detected by the sensor 1401.

Referring again to FIG. 10, the data processing terminal 1405 may include a personal computer, a portable computer including a laptop or a handheld device such as a consumer electronics device (e.g., a personal digital assistant (PDA), a telephone including a cellular phone (e.g., a multimedia and Internet-enabled mobile phone including an iPhone™, a Blackberry °, or similar phone), an mp3 player (e.g., an iPOD™, etc.), a pager, and the like), and/or a drug delivery device (e.g., an infusion device), each of which may be configured for data communication with the receiver via a wired or a wireless connection. Additionally, the data processing terminal 1405 may further be connected to a data network (not shown) for storing, retrieving, updating, and/or analyzing data corresponding to the detected analyte level of the user.

The data processing terminal 1405 may include a drug delivery device (e.g., an infusion device) such as an insulin infusion pump or the like, which may be configured to administer a drug (e.g., insulin) to the user, and which may be configured to communicate with the primary receiver unit 104 for receiving, among others, the measured analyte level. Alternatively, the primary receiver unit 1404 may be configured to integrate an infusion device therein so that the primary receiver unit 1404 is configured to administer an appropriate drug (e.g., insulin) to users, for example, for administering and modifying basal profiles, as well as for determining appropriate boluses for administration based on, among others, the detected analyte levels received from the data processing unit 1402. An infusion device may be an external device or an internal device, such as a device wholly implantable in a user.

In one embodiment, the data processing terminal 1405, which may include an infusion device, e.g., an insulin pump, may be configured to receive the analyte signals from the data processing unit 1402, and thus, incorporate the functions of the primary receiver unit 1404 including data processing for managing the user's insulin therapy and analyte monitoring. In one embodiment, the communication link 1403, as well as one or more of the other communication interfaces shown in FIG. 10, may use one or more wireless communication protocols, such as, but not limited to: an RF communication protocol, an infrared communication protocol, a Bluetooth enabled communication protocol, an 802.11x wireless communication protocol, or an equivalent wireless communication protocol which would allow secure, wireless communication of several units (for example, per Health Insurance Portability and Accountability Act (HIPPA) requirements), while avoiding potential data collision and interference.

Figure 11:
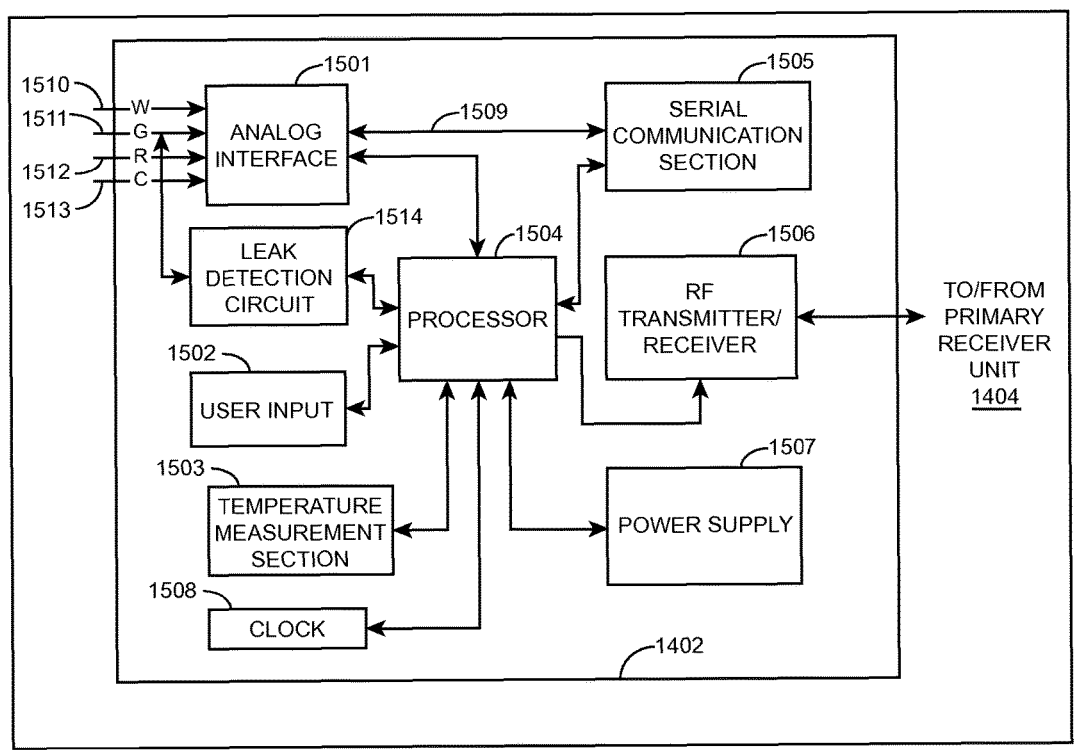
FIG. 11 illustrates a block diagram of the data processing unit 1402 shown in FIG. 10 in accordance with one embodiment.

FIG. 11 illustrates a block diagram of the data processing unit 1402 shown in FIG. 10 in accordance with one embodiment. Data processing unit 1402 includes an analog interface 1501 configured to communicate with the sensor 1401, a user input 1502, and a temperature measurement section 1503, each of which is operatively coupled to processor 1504 such as a central processing unit (CPU). Furthermore, unit 1402 is shown to include a serial communication section 1505, clock 1508, and an RF transmitter 1506, each of which is also operatively coupled to the processor 1504. Moreover, a power supply 1507 such as a battery is also provided in unit 1402 to provide the necessary power.

In another embodiment, the data processing unit may not include all components in the exemplary embodiment shown. User input and/or interface components may be included or a data processing unit may be free of user input and/or interface components. In one embodiment, one or more application-specific integrated circuits (ASIC) may be used to implement one or more functions or routines associated with the operations of the data processing unit (and/or receiver unit) using for example one or more state machines and buffers.

As can be seen in the embodiment of FIG. 11, the analyte sensor 1401 includes four contacts, three of which are electrodes: a work electrode (W) 1510, a reference electrode (R) 1512, and a counter electrode (C) 1513, each operatively coupled to the analog interface 1501 of the data processing unit 1402. This embodiment also shows an optional guard contact (G) 1511. Fewer or greater electrodes may be employed. For example, the counter and reference electrode functions may be served by a single counter/reference electrode. In some cases, there may be more than one working electrode and/or reference electrode and/or counter electrode, etc.

Figure 12:
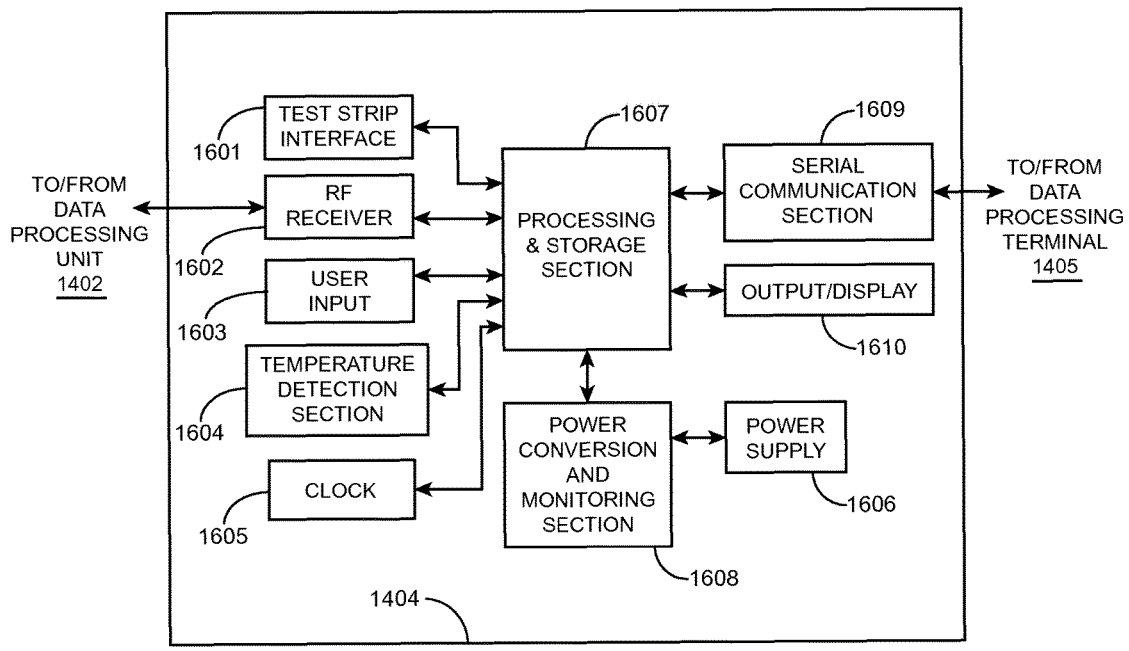
FIG. 12 illustrates a block diagram of an embodiment of a receiver/monitor unit such as the primary receiver unit 1404 of the analyte monitoring system shown in FIG. 10.

FIG. 12 illustrates a block diagram of an embodiment of a receiver/monitor unit such as the primary receiver unit 1404 of the analyte monitoring system shown in FIG. 10. The primary receiver unit 1404 includes one or more of: a test strip interface 1601, an RF receiver 1602, a user input 1603, an optional temperature detection section 1604, and a clock 1605, each of which is operatively coupled to a processing and storage section 1607. The primary receiver unit 1404 also includes a power supply 1606 operatively coupled to a power conversion and monitoring section 1608. Further, the power conversion and monitoring section 1608 is also coupled to the processing and storage section 1607. Moreover, also shown are a receiver serial communication section 1609, and an output 1610, each operatively coupled to the processing and storage section 1607. The primary receiver unit 1404 may include user input and/or interface components or may be free of user input and/or interface components.

In one embodiment, the test strip interface 1601 includes an analyte testing portion (e.g., a glucose level testing portion) to receive a blood (or other body fluid sample) analyte test or information related thereto. For example, the test strip interface 1601 may include a test strip port to receive a test strip (e.g., a glucose test strip). The device may determine the analyte level of the test strip, and optionally display (or otherwise notice) the analyte level on the output 1610 of the primary receiver unit 1404. Any suitable test strip may be employed, e.g., test strips that only require a very small amount (e.g., 3 microliters or less, e.g., 1 microliter or less, e.g., 0.5 microliters or less, e.g., 0.1 microliters or less), of applied sample to the strip in order to obtain accurate glucose information. Embodiments of test strips include, e.g., Freestyle® and Precision® blood glucose test strips from Abbott Diabetes Care, Inc. (Alameda, Calif.). Glucose information obtained by an in vitro glucose testing device may be used for a variety of purposes, computations, etc. For example, the information may be used to calibrate sensor 1401, confirm results of sensor 1401 to increase the confidence thereof (e.g., in instances in which information obtained by sensor 1401 is employed in therapy related decisions), etc.

In further embodiments, the data processing unit 1402 and/or the primary receiver unit 1404 and/or the secondary receiver unit 1406, and/or the data processing terminal/infusion device 1405 may be configured to receive the analyte value wirelessly over a communication link from, for example, a blood glucose meter. In further embodiments, a user manipulating or using the analyte monitoring system 1400 (FIG. 10) may manually input the analyte value using, for example, a user interface (for example, a keyboard, keypad, voice commands, and the like) incorporated in one or more of the data processing unit 1402, the primary receiver unit 1404, secondary receiver unit 1406, or the data processing terminal/infusion device 1405.

The features and techniques described in the present disclosure may be performed, for example, by the processing circuitry within the data processing unit 1402 or receiving unit 1404, or combination of both.

Additional detailed descriptions are provided in U.S. Pat. Nos. 5,262,035; 5,264,104; 5,262,305; 5,320,715; 5,593, 852; 6,175,752; 6,650,471; 6,746, 582, and 7,811,231, each of which is incorporated herein by reference in their entirety.

In one embodiment of the present disclosure, the analyte monitoring device includes processing circuitry that is able to determine a level of the analyte and activate an alarm system if the analyte level exceeds a threshold. The analyte monitoring device, in these embodiments, has an alarm system and may also include a display, such as an LCD or LED display.

A threshold value is exceeded if the datapoint has a value that is beyond the threshold value in a direction indicating a particular condition. For example, a datapoint which correlates to a glucose level of 200 mg/dL exceeds a threshold value for hyperglycemia of 180 mg/dL, because the datapoint indicates that the user has entered a hyperglycemic state. As another example, a datapoint which correlates to a glucose level of 65 mg/dL exceeds a threshold value for hypoglycemia of 70 mg/dL because the datapoint indicates that the user is hypoglycemic as defined by the threshold value. However, a datapoint which correlates to a glucose level of 75 mg/dL would not exceed the same threshold value for hypoglycemia because the datapoint does not indicate that particular condition as defined by the chosen threshold value.

An alarm may also be activated if the sensor readings indicate a value that is beyond a measurement range of the sensor. For glucose, the physiologically relevant measurement range may be 30-400 mg/dL, including 40-300 mg/dL and 50-250 mg/dL, of glucose in the interstitial fluid.

The alarm system may also, or alternatively, be activated when the rate of change or acceleration of the rate of change in analyte level increase or decrease reaches or exceeds a threshold rate or acceleration. For example, in the case of a in vivo positioned glucose monitor, the alarm system might be activated if the rate of change in glucose concentration exceeds a threshold value which might indicate that a hyperglycemic or hypoglycemic condition is likely to occur.

A system may also include system alarms that notify a user of system information such as battery condition, calibration, sensor dislodgment, sensor malfunction, etc. Alarms may be, for example, auditory and/or visual. Other sensory-stimulating alarm systems may be used including alarm systems which heat, cool, vibrate, or produce a mild electrical shock when activated.

Drug Delivery System

The present disclosure also includes sensors used in sensor-based drug delivery systems. The system may provide a drug to counteract the high or low level of the analyte in response to the signals from one or more sensors. Alternatively, the system may monitor the drug concentration to ensure that the drug remains within a desired therapeutic range. The drug delivery system may include one or more (e.g., two or more) sensors, a processing unit such as a transmitter, a receiver/display unit, and a drug administration system. In some cases, some or all components may be integrated in a single unit. A sensor-based drug delivery system may use data from the one or more sensors to provide necessary input for a control algorithm/mechanism to adjust the administration of drugs, e.g., automatically or semi-automatically. As an example, a glucose sensor may be used to control and adjust the administration of insulin from an external or implanted insulin pump.

Each of the various references, presentations, publications, provisional and/or non-provisional U.S. Patent Applications, U.S. Patents, non-U.S. Patent Applications, and/or non-U.S. Patents that have been identified herein, is incorporated herein by reference in its entirety.

Other embodiments and modifications within the scope of the present disclosure will be apparent to those skilled in the relevant art. Various modifications, processes, as well as numerous structures to which the embodiments of the present disclosure may be applicable will be readily apparent to those of skill in the art to which the present disclosure is directed upon review of the specification. Various aspects and features of the present disclosure may have been explained or described in relation to understandings, beliefs, theories, underlying assumptions, and/or working or prophetic examples, although it will be understood that the present disclosure is not bound to any particular understanding, belief, theory, underlying assumption, and/or working or prophetic example. Although various aspects and features of the present disclosure may have been described largely with respect to applications, or more specifically, medical applications, involving diabetic humans, it will be understood that such aspects and features also relate to any of a variety of applications involving non-diabetic humans and any and all other animals. Further, although various aspects and features of the present disclosure may have been described largely with respect to applications involving partially in vivo positioned sensors, such as transcutaneous or subcutaneous sensors, it will be understood that such aspects and features also relate to any of a variety of sensors that are suitable for use in connection with the body of an animal or a human, such as those suitable for use as fully or partially implanted in the body of an animal or a human. Finally, although the various aspects and features of the present disclosure have been described with respect to various embodiments and specific examples herein, all of which may be made or carried out conventionally, it will be understood that the invention is entitled to protection within the full scope of the appended claims.

EXAMPLE EMBODIMENTS

In some aspects of the present disclosure, methods of determining analyte trends with an analyte monitoring device are provided. The methods include receiving in vivo derived analyte measurements; calculating, with a processor, initial trends as level or non-level based on a rate-of-change for a current analyte measurement and at least one past analyte measurement. An initial trend is level when the rate-of-change is zero or within a predetermined tolerance range for zero. The method also includes determining, with the processor, whether final trends for display on a user interface are level or non-level. The final trend determinations are based on the initial trend calculations and whether a change-resistant state is active. When the change-resistant state is active, a minimum threshold of change is required between the current analyte measurement and a past analyte measurement selected as a reference in order for a final trend to transition from level to non-level. A change-resistant state is activated each time a final trend is determined to be level and deactivated each time a final trend is determined to be non-level. Further, the minimum threshold of change varies depending on the value of the current analyte measurement.

In certain embodiments, when the change-resistant state is not active, the final trend is determined to be the same as the initial trend. Further, when the change-resistant state is active and the initial trend is calculated to be level, the final trend is determined to be level. Still further, when the change-resistant state is active and the initial trend is calculated to be non-level, the minimum threshold of change is implemented to determine whether the final trend is non-level.

In certain embodiments, the methods include displaying the final trends on a display of a user interface of an analyte monitoring device.

In certain embodiments, the analyte is glucose or a ketone body.

In some aspects of the present disclosure, analyte monitoring devices are provided that include a user interface for displaying analyte trends; a processor operably coupled to the user interface; and memory operably coupled to the processor. The memory includes instructions stored therein that, when executed by the processor, cause the processor to: receive in vivo derived analyte measurements; calculate initial trends as level or non-level based on a rate-of-change for a current analyte measurement and at least one past analyte measurement; and determine whether final trends for display on the user interface are level or non-level. An initial trend is level when the rate-of-change is zero or within a predetermined tolerance range for zero. The final trend determinations are based on the initial trend calculations and whether a change-resistant state is active. Further, when the change-resistant state is active, a minimum threshold of change is required between the current analyte measurement and a past analyte measurement selected as a reference in order for a final trend to transition from level to non-level. A change-resistant state is activated each time a final trend is determined to be level and deactivated each time a final trend is determined to be non-level. Furthermore, the minimum threshold of change varies depending on the value of the current analyte measurement.

In certain embodiment, when the change-resistant state is not active, the final trend is determined to be the same as the initial trend. Further, when the change-resistant state is active and the initial trend is calculated to be level, the final trend is determined to be level. Still further, when the change-resistant state is active and the initial trend is calculated to be non-level, the minimum threshold of change is implemented to determine whether the final trend is non-level.

In certain embodiments, the memory includes instructions stored therein that, when executed by the processor, cause the processor to displaying the final trends on a display of a user interface of an analyte monitoring device.

In certain embodiments, the analyte is glucose or a ketone body.

In some aspects of the present disclosure, analyte monitoring systems are provided that include an in vivo positionable analyte sensor; sensor electronics coupled to the in vivo positionable analyte sensor; and an analyte monitoring device configured to communicate with the sensor electronics unit. The sensor electronics include a first processor and first memory operably coupled to the first processor. The analyte monitoring device includes: a user interface for displaying analyte trends; a second processor operably coupled to the user interface; and second memory operably coupled to the second processor. At least one of the first memory and second memory includes instructions stored therein that, when executed by at least one of the first and second processors, cause the at least one first and second processors to: receive in vivo derived analyte measurements; calculate initial trends as level or non-level based on a rate-of-change for a current analyte measurement and at least one past analyte measurement; and determine whether final trends for display on the user interface are level or non-level. An initial trend is level when the rate-of-change is zero or within a predetermined tolerance range for zero. The final trend determinations are based on the initial trend calculations and whether a change-resistant state is active. Further, when the change-resistant state is active, a minimum threshold of change is required between the current analyte measurement and a past analyte measurement selected as a reference in order for a final trend to transition from level to non-level. A change-resistant state is activated each time a final trend is determined to be level and deactivated each time a final trend is determined to be non-level. Furthermore, the minimum threshold of change varies depending on the value of the current analyte measurement.

In certain embodiment, when the change-resistant state is not active, the final trend is determined to be the same as the initial trend. Further, when the change-resistant state is active and the initial trend is calculated to be level, the final trend is determined to be level. Still further, when the change-resistant state is active and the initial trend is calculated to be non-level, the minimum threshold of change is implemented to determine whether the final trend is non-level.

In certain embodiments, the instructions include instructions, which when executed by at least one of the first and second processors, cause the at least one first and second processors to display the final trends on the user interface of the analyte monitoring device.

In certain embodiments, the analyte is glucose or a ketone body.

In some aspects of the present disclosure, a method of determining analyte trends with an analyte monitoring device or system is provided. The method includes receiving, with one or more processors, a series of in vivo derived analyte measurements; calculating, with the one or more processors, initial trends as level or non-level based on the series of in-vivo derived analyte measurements; and determining, with the processor, resulting analyte trends based on the initial trends and whether a change-resistant state is active. Furthermore, when the change-resistant state is active, greater changes in analyte measurements are required for a resulting analyte trend to transition from a level to non-level determination than for an initial trend to be determined as non-level.

In certain embodiments, when the change-resistant state is not active, one of a plurality of non-change-resistant states is active. In some instances, the plurality of non-change-resistant states includes a first non-change-resistant state associated with positive slopes and a second non-change-resistant state associated with negative slopes.

In certain embodiments, when the change-resistant state is not active, the resulting analyte trend is determined to be the same as the initial trend. When the change-resistant state is active and the calculated initial trend is level, the resulting analyte trend is determined to be level. When the change-resistant state is active and the calculated initial trend is non-level, an additional requirement is implemented to determine whether the resulting analyte trend is non-level. Further, the change-resistant state is activated or remains active when the resulting analyte trend is determined to be level, and deactivated or remains not active when the resulting analyte trend is determined to be non-level.

In certain embodiments, the additional requirement includes calculating, with the processor, a difference between a most recent analyte measurement and a past measurement selected as a reference; determining, with the processor, whether the difference exceeds a predetermined threshold value; determining, with the processor, that the resulting analyte trend is level when the difference does not exceed the predetermined threshold value; and determining, with the processor, that the resulting analyte trend is non-level when the difference exceeds the predetermined threshold.

In certain embodiments, the initial trend calculation includes calculating, with the processor, a difference between a most recent analyte measurement and a prior analyte measurement. The past measurement selected as a reference for the additional requirement is more recent in time than the prior analyte measurement for the initial trend calculation. For example, in one embodiment, the past measurement selected as a reference may be less than five minutes from the most recent analyte measurement, and the prior analyte measurement may be greater than or equal to five minutes from the most recent analyte measurement.

In certain embodiments, the initial trend calculation includes averaging more than one rate-of-change from a plurality of measurements from the prior analyte measurement to the most recent analyte measurement. For example, example three or more measurement may be used to average more than one rate-of-change.

In certain embodiments, the method includes displaying the resulting analyte trends on a display of a user interface.

In certain embodiments, the analyte is glucose or a ketone body.

In some aspects of the present disclosure, an analyte monitoring device that determines trends in the rate-of-change of analyte measurements is provided. The device includes a processor; and memory operably coupled to the processor. The memory includes instructions stored therein to determine analyte trends. The instructions, when executed by the processor, cause the processor to receive a series of in vivo derived analyte measurements; calculate initial trends as level or non-level based on the series of in-vivo derived analyte measurements; and determine, with the processor, resulting analyte trends based on the initial trends and whether a change-resistant state is active. Furthermore, when the change-resistant state is active, greater changes in analyte measurements are required for a resulting analyte trend to transition from a level to non-level determination than for an initial trend to be determined as non-level.

In certain embodiments, when the change-resistant state is not active, one of a plurality of non-change-resistant states is active. In some instances, the plurality of non-change-resistant states includes a first non-change-resistant state associated with positive slopes and a second non-change-resistant state associated with negative slopes.

In certain embodiments, when the change-resistant state is not active, the resulting analyte trend is determined to be the same as the initial trend. When the change-resistant state is active and the calculated initial trend is level, the resulting analyte trend is determined to be level. When the change-resistant state is active and the calculated initial trend is non-level, an additional requirement is implemented to determine whether the resulting analyte trend is non-level. Further, the change-resistant state is activated or remains active when the resulting analyte trend is determined to be level, and deactivated or remains not active when the resulting analyte trend is determined to be non-level.

In certain embodiments, the additional requirement includes calculating a difference between a most recent analyte measurement and a past measurement selected as a reference; determining whether the difference exceeds a predetermined threshold value; determining that the resulting analyte trend is level when the difference does not exceed the predetermined threshold value; and determining that the resulting analyte trend is non-level when the difference exceeds the predetermined threshold.

In certain embodiments, the initial trend calculation includes calculating a difference between a most recent analyte measurement and a prior analyte measurement. The past measurement selected as a reference for the additional requirement is more recent in time than the prior analyte measurement for the initial trend calculation. For example, in one embodiment, the past measurement selected as a reference may be less than five minutes from the most recent analyte measurement, and the prior analyte measurement may be greater than or equal to five minutes from the most recent analyte measurement.

In certain embodiments, the initial trend calculation includes averaging more than one rate-of-change from a plurality of measurements from the prior analyte measurement to the most recent analyte measurement. For example, example three or more measurement may be used to average more than one rate-of-change.

In certain embodiments, the instructions include instructions, which when executed by the processor, cause the processor to display the resulting analyte trends on a display of a user interface.

In certain embodiments, the analyte is glucose or a ketone body.

In some aspects of the present disclosure, an analyte monitoring system that determines trends in the rate-of-change of analyte measurements is provided. The system includes a sensor electronics unit and a receiver configured to communicate with the sensor electronics unit. The sensor electronics unit includes a first processor, a first memory operably coupled to the first processor, and an in vivo analyte sensor operably coupled to the first processor. The receiver includes a second processor and second memory operably coupled to the second processor. At least one of the first memory and second memory includes instructions stored therein to determine analyte trends. The instructions, when executed by at least one of the first and second processors, cause the at least one first and second processor to receive a series of in vivo derived analyte measurements; calculate initial trends as level or non-level based on the series of in-vivo derived analyte measurements; and determine, with the processor, resulting analyte trends based on the initial trends and whether a change-resistant state is active. Furthermore, when the change-resistant state is active, greater changes in analyte measurements are required for a resulting analyte trend to transition from a level to non-level determination than for an initial trend to be determined as non-level.

In certain embodiments, when the change-resistant state is not active, one of a plurality of non-change-resistant states is active. In some instances, the plurality of non-change-resistant states includes a first non-change-resistant state associated with positive slopes and a second non-change-resistant state associated with negative slopes.

In certain embodiments, when the change-resistant state is not active, the resulting analyte trend is determined to be the same as the initial trend. When the change-resistant state is active and the calculated initial trend is level, the resulting analyte trend is determined to be level. When the change-resistant state is active and the calculated initial trend is non-level, an additional requirement is implemented to determine whether the resulting analyte trend is non-level. Further, the change-resistant state is activated or remains active when the resulting analyte trend is determined to be level, and deactivated or remains not active when the resulting analyte trend is determined to be non-level.

In certain embodiments, the additional requirement includes calculating a difference between a most recent analyte measurement and a past measurement selected as a reference; determining whether the difference exceeds a predetermined threshold value; determining that the resulting analyte trend is level when the difference does not exceed the predetermined threshold value; and determining that the resulting analyte trend is non-level when the difference exceeds the predetermined threshold.

In certain embodiments, the initial trend calculation includes calculating a difference between a most recent analyte measurement and a prior analyte measurement. The past measurement selected as a reference for the additional requirement is more recent in time than the prior analyte measurement for the initial trend calculation. For example, in one embodiment, the past measurement selected as a reference may be less than five minutes from the most recent analyte measurement, and the prior analyte measurement may be greater than or equal to five minutes from the most recent analyte measurement.

In certain embodiments, the initial trend calculation includes averaging more than one rate-of-change from a plurality of measurements from the prior analyte measurement to the most recent analyte measurement. For example, example three or more measurement may be used to average more than one rate-of-change.

In certain embodiments, the instructions include instructions, which when executed by at least one of the first and second processors, cause the at least one first and second processor to display the resulting analyte trends on a display of a user interface.

In certain embodiments, the analyte is glucose or a ketone body.

In some aspects of the present disclosure, a method of selecting or modifying a response rate of an analyte monitoring device for an individual user is provided. The method includes receiving, with one or more processors, user instructions for selecting a first response rate tailored to a first user; selecting or modifying, with the one or more processors, the response rate of the analyte monitoring device to the first response rate; and operating the analyte monitoring device with the first response rate. Further, the user instructions are received externally via a user interface or a communication channel of the analyte monitoring device. Still further, the first response rate includes one or more of the following: a frequency at which data is displayed; an amount of averaging or smoothing of analyte measurement data; and a time delay for a warning or alarm.

In certain embodiments, the first response rate is tailored to physiological characteristics of the first user, the physiological characteristics comprising characteristics of the user's response to medicine or analyte absorption. For example, in one embodiment, the analyte is glucose and the medicine is insulin.

In certain embodiments, the response rate of the analyte monitoring device is increased, with the one or more processors, by performance of one or more of the following: increasing the frequency at which the data is displayed; decreasing the amount of averaging or smoothing of the analyte measurement data; and decreasing the time delay for the warning or alarm. In one embodiment, the first response rate is selected to increase the response rate of the analyte monitoring device by decreasing the amount of averaging or smoothing of analyte measurement data. In one embodiment, the first response rate is selected to increase the response rate of the analyte monitoring device for times associated with physical activity. In one embodiment, the first response rate is tailored to a critical monitoring situation of a user such that the response rate of the analyte monitoring device is increased, and wherein the critical monitoring situation is surgery or trauma procedure.

In certain embodiments, the response rate of the analyte monitoring device is decreased, with the one or more processors, by performance of one or more of the following: decreasing the frequency at which the data is displayed; increasing the amount of averaging or smoothing of the analyte measurement data; and increasing the time delay for the warning or alarm. In one embodiment, the first response rate is selected to decrease the response rate of the analyte monitoring device by increasing the amount of averaging or smoothing of analyte measurement data. In one embodiment, the response rate is decreased for times associated with sleep.

In certain embodiment, the method includes receiving, with the one or more processors, user instructions for selecting a second response rate tailored to the first user; selecting or modifying, with the one or more processors, the response rate of the analyte monitoring device to the first response rate at the corresponding times of treatment associated with the first response rate; and operating the analyte monitoring device with the first response rate at the corresponding times of treatment associated with the first response rate. The user instructions are received externally via the user interface or the communication channel of the analyte monitoring device, and the first response rate and second response rate are associated with different times of treatment. The method further includes selecting or modifying, with the one or more processors, the response rate of the analyte monitoring device to the second response rate at the corresponding times of treatment associated with the second response rate; and operating the analyte monitoring device with the second response rate at the corresponding times of treatment associated with the second response rate. The second response rate includes a frequency at which data is displayed; an amount of averaging or smoothing of analyte measurement data, and/or one or more time delays for a warning or alarm.

In certain embodiments, the method includes receiving, with the one or more processors, user instructions for selecting a third response rate tailored to a second user; selecting or modifying, with the one or more processors, the response rate of the analyte monitoring device to the third response rate; and operating the analyte monitoring device with the third response rate. The user instructions are received externally via the user interface or the communication channel of the analyte monitoring device. Further, the third response rate includes a frequency at which data is displayed; an amount of averaging or smoothing of analyte measurement data, and/or one or more time delays for a warning or alarm.

In certain embodiments, the analyte is glucose or a ketone body.

In some aspects of the present disclosure, an analyte monitoring device is provided that includes a processor and a memory operably coupled to the processor, wherein the memory includes instructions stored therein to select or modify a response rate of an analyte monitoring device for an individual user. The instructions, when executed by the processor, cause the processor to receive user instructions for selecting a first response rate tailored to a first user; select or modify the response rate of the analyte monitoring device to the first response rate; and operate the analyte monitoring device with the first response rate. The user instructions are received externally via a user interface or a communication channel of the analyte monitoring device. Further, the first response rate includes one or more of the following: a frequency at which data is displayed; an amount of averaging or smoothing of analyte measurement data; and a time delay for a warning or alarm.

In certain embodiments, the first response rate is tailored to physiological characteristics of the first user, the physiological characteristics comprising characteristics of the user's response to medicine or analyte absorption. For example, in one embodiment, the analyte is glucose and the medicine is insulin.

In certain embodiments, the response rate of the analyte monitoring device is increased by performance of one or more of the following: increasing the frequency at which the data is displayed; decreasing the amount of averaging or smoothing of the analyte measurement data; and decreasing the time delay for the warning or alarm. In one embodiment, the first response rate is selected to increase the response rate of the analyte monitoring device by decreasing the amount of averaging or smoothing of analyte measurement data. In one embodiment, the first response rate is selected to increase the response rate of the analyte monitoring device for times associated with physical activity. In one embodiment, the first response rate is tailored to a critical monitoring situation of a user such that the response rate of the analyte monitoring device is increased, and wherein the critical monitoring situation is surgery or trauma procedure.

In certain embodiments, the response rate of the analyte monitoring device is decreased by performance of one or more of the following: decreasing the frequency at which the data is displayed; increasing the amount of averaging or smoothing of the analyte measurement data; and increasing the time delay for the warning or alarm. In one embodiment, the first response rate is selected to decrease the response rate of the analyte monitoring device by increasing the amount of averaging or smoothing of analyte measurement data. In one embodiment, the response rate is decreased for times associated with sleep.

In certain embodiments, the instructions include instructions, which when executed by the processor, cause the processor to receive user instructions for selecting a second response rate tailored to the first user; select or modify the response rate of the analyte monitoring device to the first response rate at the corresponding times of treatment associated with the first response rate; and operate the analyte monitoring device with the first response rate at the corresponding times of treatment associated with the first response rate. The user instructions are received externally via the user interface or the communication channel of the analyte monitoring device, and the first response rate and second response rate are associated with different times of treatment. The instructions include instructions, which when executed by the processor, cause the processor to select or modify the response rate of the analyte monitoring device to the second response rate at the corresponding times of treatment associated with the second response rate; and operate the analyte monitoring device with the second response rate at the corresponding times of treatment associated with the second response rate. The second response rate includes a frequency at which data is displayed; an amount of averaging or smoothing of analyte measurement data, and/or one or more time delays for a warning or alarm.

In certain embodiments, the instructions include instructions, which when executed by the processor, cause the processor to receive user instructions for selecting a third response rate tailored to a second user; select or modify the response rate of the analyte monitoring device to the third response rate; and operate the analyte monitoring device with the third response rate. The user instructions are received externally via the user interface or the communication channel of the analyte monitoring device. Further, the third response rate includes a frequency at which data is displayed; an amount of averaging or smoothing of analyte measurement data, and/or one or more time delays for a warning or alarm.

In certain embodiments, the analyte is glucose or a ketone body.

In some aspects of the present disclosure, an analyte monitoring system is provided that includes a sensor electronics unit and a receiver configured to communicate with the sensor electronics unit. The sensor electronics unit includes a first processor, a first memory operably coupled to the first processor; and an in vivo analyte sensor operably coupled to the first processor. The receiver includes a second processor and second memory operably coupled to the second processor. The at least one of the first memory and second memory includes instructions stored therein to select or modify a response rate of an analyte monitoring device for an individual user. The instructions, when executed by at least one of the first and second processors, cause the at least one first and second processor to receive user instructions for selecting a first response rate tailored to a first user; select or modify the response rate of the analyte monitoring system to the first response rate; and operate the analyte monitoring system with the first response rate. The user instructions are received externally via a user interface or a communication channel of the analyte monitoring system. Further, the first response rate includes one or more of the following: a frequency at which data is displayed; an amount of averaging or smoothing of analyte measurement data; and a time delay for a warning or alarm.

In certain embodiments, the first response rate is tailored to physiological characteristics of the first user, the physiological characteristics comprising characteristics of the user's response to medicine or analyte absorption. For example, in one embodiment, the analyte is glucose and the medicine is insulin.

In certain embodiments, the response rate of the analyte monitoring system is increased by performance of one or more of the following: increasing the frequency at which the data is displayed; decreasing the amount of averaging or smoothing of the analyte measurement data; and decreasing the time delay for the warning or alarm. In one embodiment, the first response rate is selected to increase the response rate of the analyte monitoring device by decreasing the amount of averaging or smoothing of analyte measurement data. In one embodiment, the first response rate is selected to increase the response rate of the analyte monitoring system for times associated with physical activity. In one embodiment, the first response rate is tailored to a critical monitoring situation of a user such that the response rate of the analyte monitoring system is increased, and wherein the critical monitoring situation is surgery or trauma procedure.

In certain embodiments, the response rate of the analyte monitoring system is decreased by performance of one or more of the following: decreasing the frequency at which the data is displayed; increasing the amount of averaging or smoothing of the analyte measurement data; and increasing the time delay for the warning or alarm. In one embodiment, the first response rate is selected to decrease the response rate of the analyte monitoring system by increasing the amount of averaging or smoothing of analyte measurement data. In one embodiment, the response rate is decreased for times associated with sleep.

In certain embodiments, the instructions include instructions, which when executed by at least one of the first and second processors, cause the at least one first and second processor to receive user instructions for selecting a second response rate tailored to the first user; select or modify the response rate of the analyte monitoring system to the first response rate at the corresponding times of treatment associated with the first response rate; and operate the analyte monitoring system with the first response rate at the corresponding times of treatment associated with the first response rate. The user instructions are received externally via the user interface or the communication channel of the analyte monitoring system, and the first response rate and second response rate are associated with different times of treatment. The instructions include instructions, which when executed by at least one of the first and second processors, cause the at least one first and second processor to select or modify the response rate of the analyte monitoring system to the second response rate at the corresponding times of treatment associated with the second response rate; and operate the analyte monitoring system with the second response rate at the corresponding times of treatment associated with the second response rate. The second response rate includes a frequency at which data is displayed; an amount of averaging or smoothing of analyte measurement data, and/or one or more time delays for a warning or alarm.

In certain embodiments, the instructions include instructions, which when executed by at least one of the first and second processors, cause the at least one first and second processor to receive user instructions for selecting a third response rate tailored to a second user; select or modify the response rate of the analyte monitoring system to the third response rate; and operate the analyte monitoring system with the third response rate. The user instructions are received externally via the user interface or the communication channel of the analyte monitoring system. Further, the third response rate includes a frequency at which data is displayed; an amount of averaging or smoothing of analyte measurement data, and/or one or more time delays for a warning or alarm.

In certain embodiments, the analyte is glucose or a ketone body.

It should be understood that techniques introduced above can be implemented by programmable circuitry programmed or configured by software and/or firmware, or they can be implemented entirely by special-purpose "hardwired" circuitry, or in a combination of such forms. Such special-purpose circuitry (if any) can be in the form of, for example, one or more application-specific integrated circuits (ASICS), programmable logic devices (PLDs), field-programmable gate arrays (FPGAs), etc.

Software or firmware implementing the techniques introduced herein may be stored on a machine-readable storage medium and may be executed by one or more general-purpose or special-purpose programmable microprocessors. A "machine-readable medium", as the term is used herein, includes any mechanism that can store information in a form accessible by a machine (a machine may be, for example, a computer, network device, cellular phone, personal digital assistant (PDA), manufacturing took, any device with one or more processors, etc.). For example, a machine-accessible medium includes recordable/non-recordable media (e.g., read-only memory (ROM); random access memory (RAM); magnetic disk storage media; optical storage media; flash memory devices; etc.), etc.

Furthermore, a data processing device or system, such as a computer or computer system may be configured to execute some of the techniques introduced herein. The computer may include, for example, a processing device, memory with instructions stored therein to perform the techniques, input/output device elements (e.g., a monitor, keyboard, etc.), etc. For example, the device or system may be used to configure, calibrate, or otherwise program an analyte monitoring device intended to perform analyte measurements, such as analyte point measurements and/or analyte rate-of-change measurements. In some aspects of the present disclosure, some of the techniques described herein may be provided to the device or system from an article of manufacture including the machine readable medium described above.

The preceding examples are put forth so as to provide those of ordinary skill in the art with a complete disclosure and description of how to make and use the embodiments of the invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

That which is claimed is:

1. A method comprising:
   repeatedly receiving, with a processor of an analyte monitoring device, in vivo derived analyte measurements of an analyte, wherein the analyte is glucose or a ketone body;
   calculating, with the processor, an initial analyte trend as level or non-level based on a rate-of-change for a current analyte measurement of the analyte measurements and at least one past analyte measurement of the analyte measurements, wherein the initial analyte trend is level when the rate-of-change is zero or within a predetermined tolerance range for zero; and
   determining, with the processor, whether a final analyte trend for display via a user interface is level or non-level, wherein the final analyte trend determination is based on the initial analyte trend and whether a change-resistant state is active;
   wherein when the change-resistant state is active, a minimum threshold of change is required between the current analyte measurement and a past analyte measurement of the analyte measurements selected as a reference for the final analyte trend to be determined as non-level when a previous final analyte trend was determined to be level;
   wherein the change-resistant state is activated when the final analyte trend is determined to be level and deactivated when the final analyte trend is determined to be non-level; and
   wherein the minimum threshold of change varies based on the current analyte measurement.

2. The method of claim 1, wherein when the change-resistant state is not active, the final analyte trend is determined to be the same as the initial analyte trend;
   wherein when the change-resistant state is active and the initial analyte trend is calculated to be level, the final analyte trend is determined to be level; and
   wherein when the change-resistant state is active and the initial analyte trend is calculated to be non-level, the minimum threshold of change is implemented to determine whether the final analyte trend is non-level.

3. The method of claim 1, further comprising displaying the final analyte trend via the user interface on a display of the analyte monitoring device.

4. The method of claim 1, wherein when the change resistant state is active and the initial analyte trend is determined to be level, the final analyte trend is determined to be level and is displayed.

5. The method of claim 4, wherein the change resistant state remains active.

6. The method of claim 1, wherein the final analyte trend is determined to be level when:
   the change resistant state is active,
   the initial analyte trend is determined to be non-level, and
   the minimum threshold of change is not exceeded between the current analyte measurement and the past analyte measurement selected as the reference.

7. The method of claim 5, wherein the change resistant state remains active.

8. The method of claim 1, wherein the final analyte trend is determined to be level when:
   the change resistant state is active,
   the initial analyte trend is determined to be non-level, and
   the minimum threshold of change is not exceeded between the current analyte measurement and the past analyte measurement selected as the reference.

9. The method of claim 8, wherein the change resistant state is deactivated.

10. The method of claim 1, wherein when the change resistant state is not active and the initial analyte trend is determined to be level, the final analyte trend is determined to be level and is displayed.

11. The method of claim 10, wherein the change resistant state is activated.

12. The method of claim 1, wherein when the change resistant state is not active and the initial analyte trend is determined to be non-level, the final analyte trend is determined to be non-level and is displayed.

13. The method of claim 12, wherein the change resistant state remains not active.

14. An analyte monitoring device, comprising:
a display for displaying glucose or ketone body analyte trends via a user interface;
a processor operably coupled to the display; and
memory operably coupled to the processor, wherein the memory includes instructions stored therein that, when executed by the processor, cause the processor to:
repeatedly receive in vivo derived analyte measurements of an analyte from an in vivo analyte sensor, wherein the analyte is glucose or a ketone body;
calculate an initial analyte trend as level or non-level based on a rate-of-change for a current analyte measurement of the analyte measurements and at least one past analyte measurement of the analyte measurements, wherein the initial analyte trend is level when the rate-of-change is zero or within a predetermined tolerance range for zero; and
determine whether a final analyte trend for display via the user interface is level or non-level, wherein the final analyte trend determination is based on the initial analyte trend and whether a change-resistant state is active;
wherein when the change-resistant state is active, a minimum threshold of change is required between the current analyte measurement and a past analyte measurement of the analyte measurements selected as a reference for the final analyte trend to be determined as non-level when a previous final analyte trend was determined to be level;
wherein the change-resistant state is activated when the final analyte trend is determined to be level and deactivated when the final analyte trend is determined to be non-level; and
wherein the minimum threshold of change varies based on the current analyte measurement.

15. The analyte monitoring device of claim 14, wherein when the change-resistant state is not active, the final analyte trend is determined to be the same as the initial analyte trend;
wherein when the change-resistant state is active and the initial analyte trend is calculated to be level, the final analyte trend is determined to be level; and
wherein when the change-resistant state is active and the initial analyte trend is calculated to be non-level, the minimum threshold of change is implemented to determine whether the final analyte trend is non-level.

16. The analyte monitoring device of claim 14, wherein the instructions include instructions that, when executed by the processor, cause the processor to display the final analyte trend via the user interface on the display of the analyte monitoring device.

17. The analyte monitoring device of claim 14, wherein the memory includes instructions stored therein that, when executed by the processor, cause the processor to determine the final analyte trend is level when the change resistant state is active and the initial analyte trend is determined to be level.

18. The analyte monitoring device of claim 17, wherein the change resistant state remains active.

19. The analyte monitoring device of claim 14, wherein the memory includes instructions stored therein that, when executed by the processor, cause the processor to determine the final analyte trend is level when:
the change resistant state is active,
the initial analyte trend is determined to be non-level, and
the minimum threshold of change is not exceeded between the current analyte measurement and the past analyte measurement selected as the reference.

20. The analyte monitoring device of claim 19, wherein the change resistant state remains active.

21. The analyte monitoring device of claim 14, wherein the memory includes instructions stored therein that, when executed by the processor, cause the processor to determine the final analyte trend is non-level when:
the change resistant state is active,
the initial analyte trend is determined to be non-level, and
the minimum threshold of change is not exceeded between the current analyte measurement and the past analyte measurement selected as the reference.

22. The analyte monitoring device of claim 21, wherein the change resistant state is deactivated.

23. The analyte monitoring device of claim 14, wherein the memory includes instructions stored therein that, when executed by the processor, cause the processor to determine the final analyte trend is level when the change resistant state is not active and the initial analyte trend is determined to be level.

24. The analyte monitoring device of claim 23, wherein the change resistant state is activated.

25. The analyte monitoring device of claim 14, wherein the memory includes instructions stored therein that, when executed by the processor, cause the processor to determine the final analyte trend is non-level when the change resistant state is not active and the initial analyte trend is determined to be non-level.

26. The analyte monitoring device of claim 25, wherein the change resistant state remains not active.

27. An analyte monitoring system, comprising:
an in vivo positionable analyte sensor;
sensor electronics coupled to the in vivo positionable analyte sensor comprising: a first processor and first memory operably coupled to the first processor; and
an analyte monitoring device configured to communicate with the sensor electronics, the analyte monitoring device comprising: a display for displaying analyte trends via a user interface, a second processor operably coupled to the display, and second memory operably coupled to the second processor;
wherein at least one of the first memory and second memory includes instructions stored therein that, when executed by at least one of the first processor or the second processor, cause the at least one of the first processor or the second processor to:
receive in vivo derived analyte measurements of an analyte from the in vivo positionable analyte sensor, wherein the analyte is glucose or a ketone body;
calculate an initial analyte trend as level or non-level based on a rate-of-change for a current analyte measurement of the analyte measurements and at least one past analyte measurement of the analyte measurements, wherein the initial analyte trend is level when the rate-of-change is zero or within a predetermined tolerance range for zero; and determine whether a final analyte trend for display via the user interface is level or non-level, wherein the final analyte trend determination is based on the initial analyte trend and whether a change-resistant state is active;

wherein when the change-resistant state is active, a minimum threshold of change is required between the current analyte measurement and a past analyte measurement of the analyte measurements selected as a reference for the final analyte trend to be determined as non-level when a previous final analyte trend was determined to be level;

wherein the change-resistant state is activated when the final analyte trend is determined to be level and deactivated when the final analyte trend is determined to be non-level; and wherein the minimum threshold of change varies based on the current analyte measurement.

28. The analyte monitoring system of claim 27, wherein when the change-resistant state is not active, the final analyte trend is determined to be the same as the initial analyte trend;

wherein when the change-resistant state is active and the initial analyte trend is calculated to be level, the final analyte trend is determined to be level; and wherein when the change-resistant state is active and the initial analyte trend is calculated to be non-level, the minimum threshold of change is implemented to determine whether the final analyte trend is non-level.

29. The analyte monitoring system of claim 27, wherein the instructions include instructions that, when executed by the at least one of the first processor or the second processor, cause the at least one of the first processor or the second processor to display the final analyte trend via the user interface on the display of the analyte monitoring device.

* * * * *